(12) United States Patent
Worrell et al.

(10) Patent No.: US 9,089,327 B2
(45) Date of Patent: Jul. 28, 2015

(54) SURGICAL INSTRUMENT WITH MULTI-PHASE TRIGGER BIAS

(71) Applicant: Ethicon Endo-Surgery Inc., Cincinnati, OH (US)

(72) Inventors: Barry C. Worrell, Centerville, OH (US); Jason R. Lesko, Harrison, OH (US); Bingshi Wang, Mason, OH (US); Carl J. Draginoff, Jr., Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 260 days.

(21) Appl. No.: 13/622,729

(22) Filed: Sep. 19, 2012

(65) Prior Publication Data

US 2013/0030428 A1    Jan. 31, 2013

Related U.S. Application Data

(63) Continuation-in-part of application No. 13/235,623, filed on Sep. 19, 2011.

(60) Provisional application No. 61/386,094, filed on Sep. 24, 2010.

(51) Int. Cl.
    *A61B 18/14*      (2006.01)
    *A61B 17/072*     (2006.01)
    (Continued)

(52) U.S. Cl.
    CPC ......... *A61B 17/07207* (2013.01); *A61B 5/0205* (2013.01); *A61B 18/1445* (2013.01); *A61B 18/1447* (2013.01); *A61B 2017/0038* (2013.01);
    (Continued)

(58) Field of Classification Search
    CPC .................. A61B 18/1447; A61B 18/1445
    USPC ....................................... 606/51, 52
    See application file for complete search history.

(56) References Cited

U.S. PATENT DOCUMENTS 2,715,341 A    8/1955  Hogan
2,818,744 A    1/1958  Moody
(Continued)

FOREIGN PATENT DOCUMENTS

DE    43 00 307     7/1994
EP    1637086       3/2006
(Continued)

OTHER PUBLICATIONS

International Search Report dated Jan. 30, 2014 for Application No. PCT/US2013/060537.
(Continued)

*Primary Examiner* — George Evanisko
(74) *Attorney, Agent, or Firm* — Frost Brown Todd LLC

(57) ABSTRACT

An apparatus comprises an end effector, an elongate shaft, and a handle assembly. The end effector is operable to grasp tissue. The elongate shaft extends between the end effector and the handle assembly. The handle assembly comprises a body portion, a trigger, and a trigger return lever. The trigger is movable relative to the body portion from a home position to an actuated position, and is thereby operable to control the end effector to selectively grasp tissue. The trigger includes a cam feature. The trigger return lever is positioned to engage the cam feature of the trigger. The trigger return lever is configured to bias the trigger toward the home position during at least part of a range of motion of the trigger from the home position to the actuated position.

20 Claims, 25 Drawing Sheets

(51) Int. Cl.
*A61B 5/0205* (2006.01)
*A61B 17/00* (2006.01)
*A61B 17/29* (2006.01)
*A61B 18/00* (2006.01)

(52) U.S. Cl.
CPC . *A61B 2017/2908* (2013.01); *A61B 2017/2927* (2013.01); *A61B 2017/2946* (2013.01); *A61B 2018/00642* (2013.01); *A61B 2018/00678* (2013.01); *A61B 2018/00702* (2013.01); *A61B 2018/00755* (2013.01); *A61B 2018/00767* (2013.01); *A61B 2018/00791* (2013.01); *A61B 2018/00815* (2013.01); *A61B 2018/00898* (2013.01); *A61B 2018/1455* (2013.01)

(56) References Cited

U.S. PATENT DOCUMENTS

| | | |
|---|---|---|
| 2,857,776 A | 10/1958 | Williams |
| 2,881,645 A | 4/1959 | Kruchten |
| 3,194,530 A | 7/1965 | Heyl |
| 4,203,430 A | 5/1980 | Takahashi |
| 4,483,562 A | 11/1984 | Schoolman |
| 4,723,936 A | 2/1988 | Buchbinder et al. |
| 4,880,015 A | 11/1989 | Nierman |
| 4,945,920 A | 8/1990 | Clossick |
| 5,020,514 A | 6/1991 | Heckele |
| 5,125,895 A | 6/1992 | Buchbinder et al. |
| 5,171,249 A * | 12/1992 | Stefanchik et al. ........... 606/142 |
| 5,330,502 A | 7/1994 | Hassler et al. |
| 5,383,888 A | 1/1995 | Zvenyatsky et al. |
| 5,391,180 A | 2/1995 | Tovey et al. |
| 5,395,329 A | 3/1995 | Fleischhacker et al. |
| 5,409,498 A | 4/1995 | Braddock et al. |
| 5,411,519 A | 5/1995 | Tovey et al. |
| 5,441,499 A | 8/1995 | Fritzsch |
| 5,454,827 A | 10/1995 | Aust et al. |
| 5,462,546 A | 10/1995 | Rydell |
| 5,514,130 A | 5/1996 | Baker |
| 5,514,157 A | 5/1996 | Nicholas et al. |
| 5,540,685 A | 7/1996 | Parins et al. |
| 5,549,637 A | 8/1996 | Crainich |
| 5,562,682 A | 10/1996 | Oberlin et al. |
| 5,582,617 A | 12/1996 | Klieman et al. |
| 5,607,450 A | 3/1997 | Zvenyatsky et al. |
| 5,609,601 A | 3/1997 | Kolesa et al. |
| 5,626,587 A | 5/1997 | Bishop et al. |
| 5,632,432 A | 5/1997 | Schulze et al. |
| 5,643,294 A | 7/1997 | Tovey et al. |
| 5,700,275 A | 12/1997 | Bell et al. |
| 5,704,534 A | 1/1998 | Huitema et al. |
| 5,743,456 A | 4/1998 | Jones et al. |
| 5,766,196 A | 6/1998 | Griffiths |
| 5,766,205 A | 6/1998 | Zvenyatsky et al. |
| 5,782,859 A | 7/1998 | Nicholas et al. |
| 5,833,695 A | 11/1998 | Yoon |
| 5,921,956 A | 7/1999 | Grinberg et al. |
| 5,931,832 A | 8/1999 | Jensen |
| 6,010,054 A | 1/2000 | Johnson et al. |
| 6,162,208 A | 12/2000 | Hipps |
| 6,179,809 B1 | 1/2001 | Khairkhahan et al. |
| 6,423,059 B1 | 7/2002 | Hanson et al. |
| 6,500,176 B1 | 12/2002 | Truckai et al. |
| 6,554,794 B1 | 4/2003 | Mueller et al. |
| RE38,335 E | 11/2003 | Aust et al. |
| 6,783,524 B2 | 8/2004 | Anderson et al. |
| 6,991,627 B2 | 1/2006 | Madhani et al. |
| 7,004,938 B2 | 2/2006 | Ormsby et al. |
| 7,055,731 B2 | 6/2006 | Shelton et al. |
| 7,070,595 B2 | 7/2006 | Ormsby et al. |
| 7,081,114 B2 | 7/2006 | Rashidi |
| 7,087,071 B2 | 8/2006 | Nicholas et al. |
| 7,112,201 B2 | 9/2006 | Truckai et al. |
| 7,125,409 B2 | 10/2006 | Truckai et al. |
| 7,128,254 B2 | 10/2006 | Shelton et al. |
| 7,141,897 B2 | 11/2006 | Park |
| 7,143,925 B2 | 12/2006 | Shelton et al. |
| 7,150,749 B2 | 12/2006 | Dycus et al. |
| 7,156,846 B2 | 1/2007 | Dycus et al. |
| 7,159,750 B2 | 1/2007 | Racenet et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,208,005 B2 | 4/2007 | Frecker et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,407,076 B2 | 8/2008 | Racenet et al. |
| 7,424,965 B2 | 9/2008 | Racenet et al. |
| 7,455,208 B2 | 11/2008 | Wales et al. |
| 7,464,849 B2 | 12/2008 | Shelton, IV et al. |
| 7,481,348 B2 | 1/2009 | Marczyk |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,540,872 B2 | 6/2009 | Schechter et al. |
| 7,549,564 B2 | 6/2009 | Boudreaux |
| 7,553,275 B2 | 6/2009 | Padget et al. |
| 7,559,450 B2 | 7/2009 | Wales et al. |
| 7,584,880 B2 | 9/2009 | Racenet et al. |
| 7,594,913 B2 | 9/2009 | Ormsby et al. |
| 7,597,230 B2 | 10/2009 | Racenet et al. |
| 7,615,044 B2 | 11/2009 | Scheibe et al. |
| 7,654,431 B2 | 2/2010 | Hueil et al. |
| 7,691,095 B2 | 4/2010 | Bednarek et al. |
| 7,703,653 B2 | 4/2010 | Shah et al. |
| 7,708,182 B2 | 5/2010 | Viola |
| 7,721,935 B2 | 5/2010 | Racenet et al. |
| 7,771,425 B2 | 8/2010 | Dycus et al. |
| 7,780,054 B2 | 8/2010 | Wales |
| 7,784,662 B2 | 8/2010 | Wales et al. |
| 7,793,814 B2 | 9/2010 | Racenet et al. |
| 7,798,386 B2 | 9/2010 | Schall et al. |
| 7,799,028 B2 | 9/2010 | Schechter et al. |
| 7,815,090 B2 | 10/2010 | Marczyk |
| 7,815,091 B2 | 10/2010 | Marczyk |
| 7,815,637 B2 | 10/2010 | Ormsby et al. |
| 7,828,725 B2 | 11/2010 | Maruyama |
| 7,842,025 B2 | 11/2010 | Coleman et al. |
| 7,909,220 B2 | 3/2011 | Viola |
| 8,006,365 B2 | 8/2011 | Levin et al. |
| 8,033,441 B2 | 10/2011 | Marczyk |
| 8,062,306 B2 | 11/2011 | Nobis et al. |
| 8,092,451 B2 | 1/2012 | Schechter et al. |
| 8,100,309 B2 | 1/2012 | Marczyk |
| 8,142,473 B2 | 3/2012 | Cunningham |
| 8,152,799 B2 | 4/2012 | Ormsby et al. |
| 8,161,838 B2 | 4/2012 | Duval |
| 8,197,479 B2 | 6/2012 | Olson et al. |
| 8,205,619 B2 | 6/2012 | Shah et al. |
| 8,236,010 B2 | 8/2012 | Ortiz et al. |
| 8,241,320 B2 | 8/2012 | Lyons et al. |
| 8,292,147 B2 | 10/2012 | Viola |
| 8,292,889 B2 | 10/2012 | Cunningham et al. |
| 8,308,659 B2 | 11/2012 | Scheibe et al. |
| 8,317,811 B2 | 11/2012 | Laporte Rosello et al. |
| 8,323,239 B2 | 12/2012 | Bednarek et al. |
| 8,323,297 B2 | 12/2012 | Hinman et al. |
| 8,353,902 B2 | 1/2013 | Prakash |
| 8,357,161 B2 | 1/2013 | Mueller |
| 8,361,067 B2 | 1/2013 | Pellegrino et al. |
| 8,366,709 B2 | 2/2013 | Schechter et al. |
| 8,372,064 B2 | 2/2013 | Douglass et al. |
| 8,403,832 B2 | 3/2013 | Cunningham et al. |
| 8,403,945 B2 | 3/2013 | Whitfield et al. |
| 8,789,741 B2 | 7/2014 | Baxter et al. |
| 2003/0163085 A1 | 8/2003 | Tanner et al. |
| 2006/0259071 A1 | 11/2006 | Nicholas et al. |
| 2007/0043353 A1 | 2/2007 | Dycus et al. |
| 2007/0219550 A1 | 9/2007 | Thompson et al. |

(56) References Cited

U.S. PATENT DOCUMENTS

| | | |
|---|---|---|
| 2007/0282324 A1 | 12/2007 | Vaska et al. |
| 2008/0161798 A1 | 7/2008 | Podmore et al. |
| 2009/0125019 A1 | 5/2009 | Douglass et al. |
| 2009/0198272 A1 | 8/2009 | Kerver et al. |
| 2009/0283568 A1 | 11/2009 | Racenet et al. |
| 2010/0094289 A1 | 4/2010 | Taylor et al. |
| 2010/0179540 A1 | 7/2010 | Maeczyk et al. |
| 2010/0179545 A1 | 7/2010 | Twomey et al. |
| 2010/0193566 A1 | 8/2010 | Scheib et al. |
| 2010/0249759 A1 | 9/2010 | Hinman et al. |
| 2010/0298824 A1 | 11/2010 | Rothstein et al. |
| 2011/0009863 A1 | 1/2011 | Marczyk et al. |
| 2011/0087218 A1 | 4/2011 | Boudreaux et al. |
| 2011/0184459 A1 | 7/2011 | Malkowski et al. |
| 2011/0213360 A1 | 9/2011 | Cunningham et al. |
| 2011/0213361 A1 | 9/2011 | Cunningham et al. |
| 2011/0213363 A1 | 9/2011 | Cunningham et al. |
| 2011/0230875 A1 | 9/2011 | Walberg et al. |
| 2011/0264074 A1 | 10/2011 | Tegg et al. |
| 2011/0282176 A1 | 11/2011 | Tegg |
| 2012/0074200 A1 | 3/2012 | Schmid et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0109186 A1 | 5/2012 | Parrott et al. |
| 2012/0116379 A1 | 5/2012 | Yates et al. |
| 2012/0143088 A1 | 6/2012 | Schultz |
| 2012/0179151 A1 | 7/2012 | Mueller |
| 2012/0203169 A1 | 8/2012 | Tegg |
| 2012/0215220 A1 | 8/2012 | Kerver et al. |
| 2012/0253326 A1 | 10/2012 | Kleyman |
| 2012/0265186 A1 | 10/2012 | Burger et al. |
| 2012/0303013 A1 | 11/2012 | Burell et al. |
| 2012/0316560 A1 | 12/2012 | Hassoun |
| 2013/0012929 A1 | 1/2013 | Malkowski |
| 2013/0012986 A1 | 1/2013 | Suzuki |
| 2013/0026868 A1 | 1/2013 | Klafter et al. |
| 2013/0032627 A1 | 2/2013 | Viola |
| 2013/0041403 A1 | 2/2013 | Cunningham et al. |
| 2013/0096407 A1 | 4/2013 | Bednarek et al. |

FOREIGN PATENT DOCUMENTS

| | | |
|---|---|---|
| EP | 2151204 | 2/2010 |
| EP | 2 198 787 | 6/2010 |
| FR | 2 915 873 | 11/2008 |
| WO | WO 00/67834 | 11/2000 |
| WO | WO 2008/045348 | 4/2008 |
| WO | WO 2010/104755 | 9/2010 |
| WO | WO 2011/044343 | 4/2011 |
| WO | WO 2012/067468 | 5/2012 |
| WO | WO 2012/078951 | 6/2012 |

OTHER PUBLICATIONS

International Search Report dated Jan. 31, 2014 for Application No. PCT/US2013/060536.
Abstract and Machine Translation of German Patent No. DE 43 00 307.
Abstract and Machine Translation of French Patent No. FR 2 915 873.
International Search Report dated Jun. 13, 2012 for Application No. PCT/US2011/053016.
U.S. Appl. No. 13/622,735, filed Sep. 19, 2012, Worrell et al.
International Search Report dated Dec. 16, 2011 for Application No. PCT/US2011/052707.
International Search Report dated Dec. 28, 2011 for Application No. PCT/US2011/052712.
International Search Report and Written Opinion dated Jan. 24, 2012 for Application No. PCT/US2011/052734.
International Search Report dated Mar. 19, 2012 for Application No. PCT/US2011/053028.
Office Action Non-Final for dated Aug. 15, 2014 for U.S. Appl. No. 13/235,623.
Restriction Requirement dated Sep. 4, 2014 for U.S. Appl. No. 13/235,648.
U.S. Appl. No. 61/410,603, filed Nov. 5, 2010.
Australian Examiner's Report dated Aug. 15, 2013 for Application No. AU 2011305198, 6 pages.
Australian Examiner's Report dated Aug. 14, 2013 for Application No. AU 2011305205, 4 pages.
Australian Examiner's Report dated Aug. 8, 2013 for Application No. AU 2011305397, 5 pages.
Chinese First Office Action dated Dec. 17, 2014 for Application No. CN 2011800460673, 13 pages.
International Written Opinion dated Dec. 16, 2011 for Application No. PCT/US2011/052707, 7 pages.
International Written Opinion dated Dec. 28, 2011 for Application No. PCT/US2011/05712, 8 pages.
International Written Opinion dated Jun. 13, 2012 for Application No. PCT/US2011/053016, 8 pages.
International Written Opinion dated Mar. 19, 2012 for Application No. PCT/US2011/053028, 7 pages.
International Written Opinion dated Jan. 31, 2014 for Application No. PCT/US2013/060536, 5 pages.
International Written Opinion dated Jan. 30, 2014 for Application No. PCT/US2013/060537, 5 pages.
US Office Action, Non-Final, dated Dec. 19, 2014 for U.S. Appl. No. 13/622,735, 7 pages.

* cited by examiner

SURGICAL INSTRUMENT WITH MULTI-PHASE TRIGGER BIAS

PRIORITY

This application is a continuation-in-part of U.S. application Ser. No. 13/235,623, entitled "Control Features for Articulating Surgical Device," filed Sep. 19, 2011 and now published as U.S. Pub. No. 2012/0078243, the disclosure of which is incorporated by reference herein, and which claims priority to U.S. Provisional Application Ser. No. 61/386,094, filed Sep. 24, 2010, entitled "Articulating Surgical Device," the disclosure of which is incorporated by reference herein.

BACKGROUND

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; and U.S. Pub. No. 2012/0116379, entitled "Motor Driven Electrosurgical Device with Mechanical and Electrical Feedback," published May 10, 2012, the disclosure of which is incorporated by reference herein.

In addition, a variety of surgical instruments include a shaft having an articulation section, providing enhanced positioning capabilities for an end effector that is located distal to the articulation section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
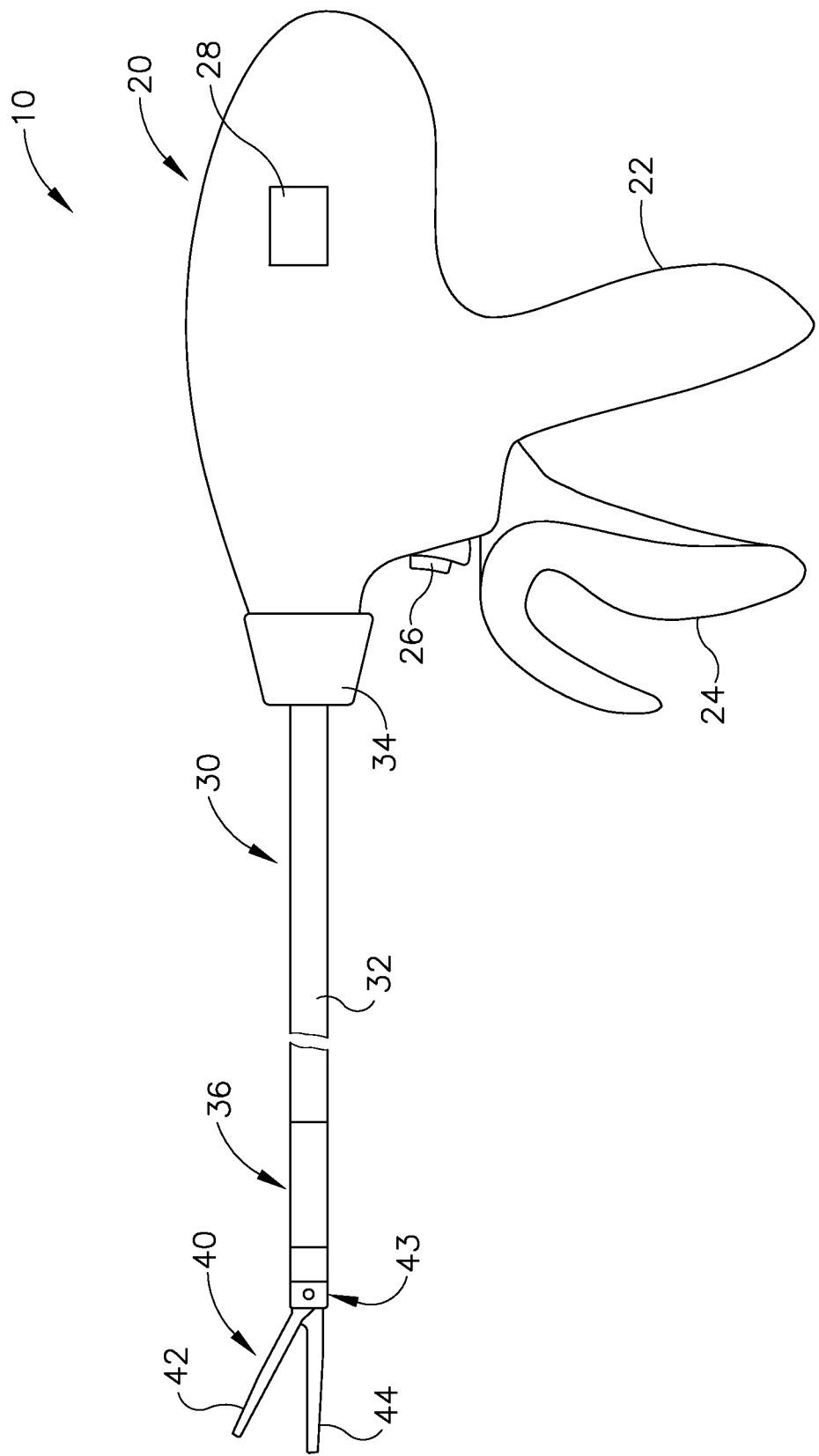
FIG. 1 depicts a side elevational view of an exemplary electrosurgical medical device.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, issued as U.S. Pat. No. 8,939,974; and/or U.S. Pub. No. 2012/0116379. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24)

cannot be fully actuated unless button (26) is being pressed simultaneously. Examples of how such a lockout may be provided are disclosed in one or more of the references cited herein. It should be understood that pistol grip (22), trigger (24), and button (26) may be modified, substituted, supplemented, etc. in any suitable way, and that the descriptions of such components herein are merely illustrative. Articulation control (28) of the present example is operable to selectively control articulation section (36) of shaft (30), which will be described in greater detail below. Various examples of forms that articulation control (28) may take will also be described in greater detail below, while further examples will be apparent to those of ordinary skill in the art in view of the teachings herein.

Shaft (30) of the present example includes an outer sheath (32) and an articulation section (36). Articulation section (36) is operable to selectively position end effector (40) at various angles relative to the longitudinal axis defined by sheath (32). Various examples of forms that articulation section (36) and other components of shaft (30) may take will be described in greater detail below, while further examples will be apparent to those of ordinary skill in the art in view of the teachings herein. For instance, it should be understood that various components that are operable to actuate articulation section (36) may extend through the interior of sheath (32). In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating any portion of shaft (30) that is proximal of articulation section (36). Other suitable rotation schemes will be apparent to those of ordinary skill in the art in view of the teachings herein. Of course, rotatable features may simply be omitted if desired.

B. Exemplary End Effector

End effector (40) of the present example comprises a first jaw (42) and a second jaw (44). In the present example, second jaw (44) is substantially fixed relative to shaft (30); while first jaw (42) pivots relative to shaft (30), toward and away from second jaw (42). In some versions, actuators such as rods or cables, etc., may extend through sheath (32) and be joined with first jaw (42) at a pivotal coupling (43), such that longitudinal movement of the actuator rods/cables/etc. through shaft (30) provides pivoting of first jaw (42) relative to shaft (30) and relative to second jaw (44). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
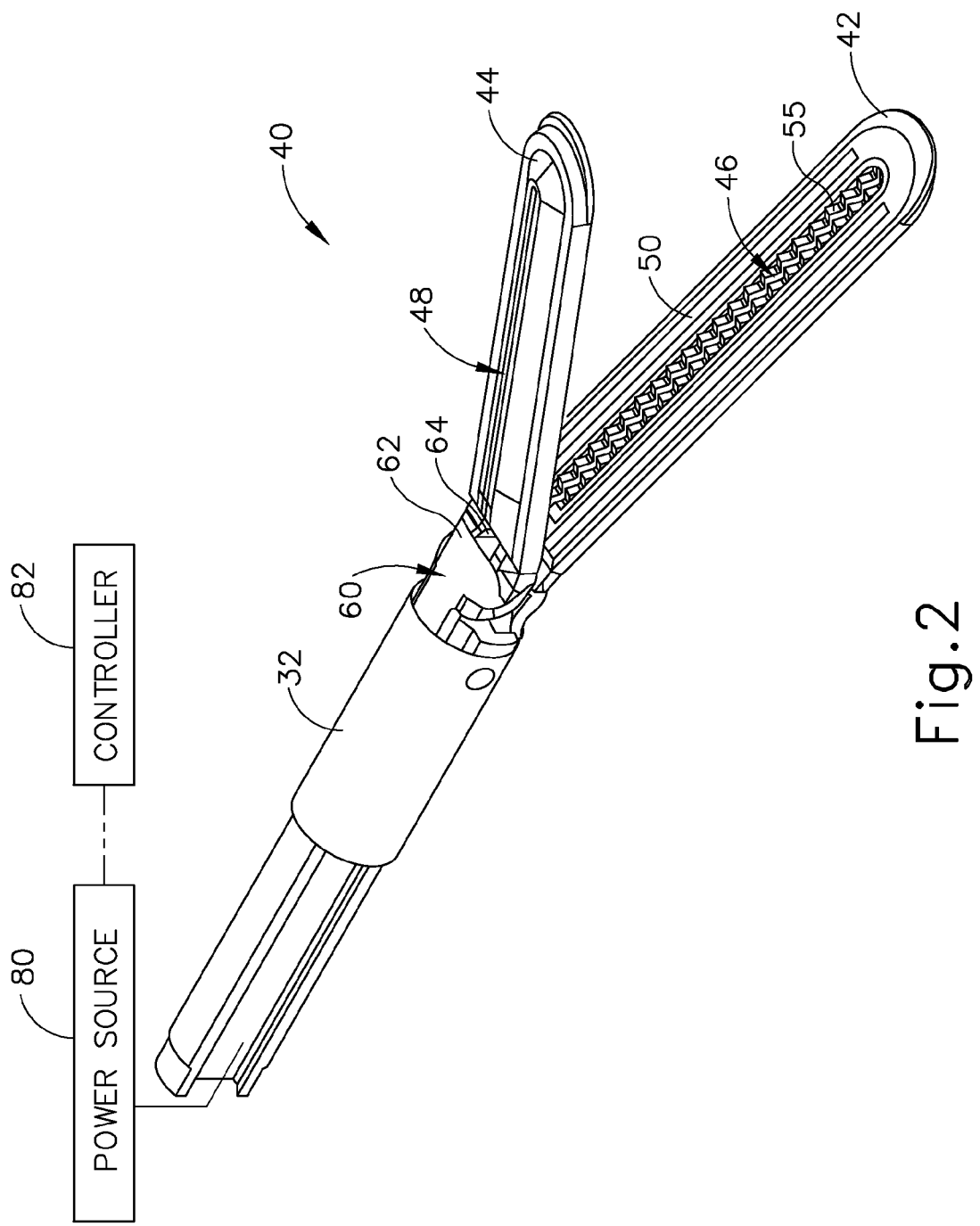
FIG. 2 depicts a perspective view of the end effector of the device of FIG. 1, in an open configuration.
Figure 3:
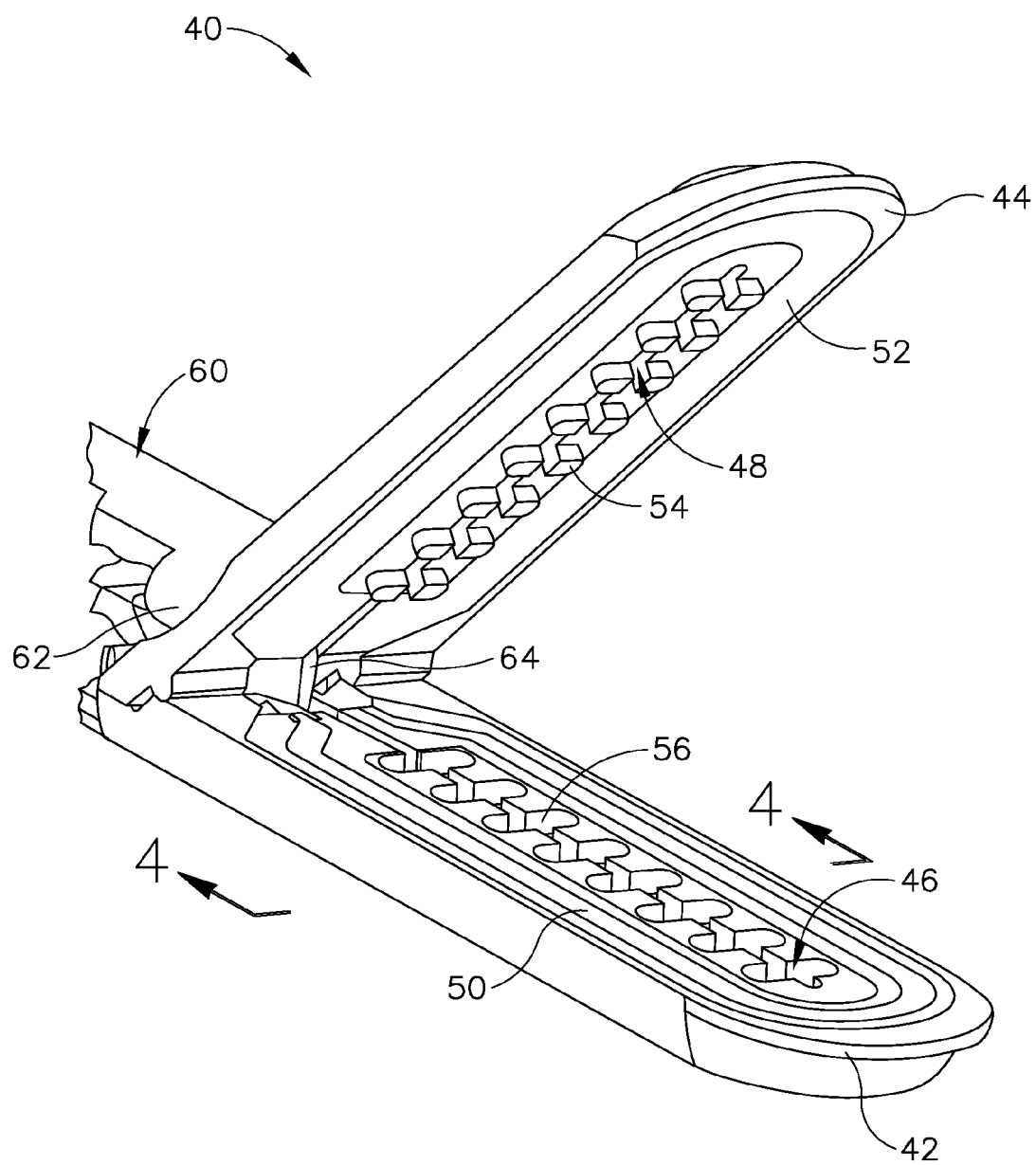
FIG. 3 depicts another perspective view of the end effector of the device of FIG. 1, in an open configuration.
Figure 4:
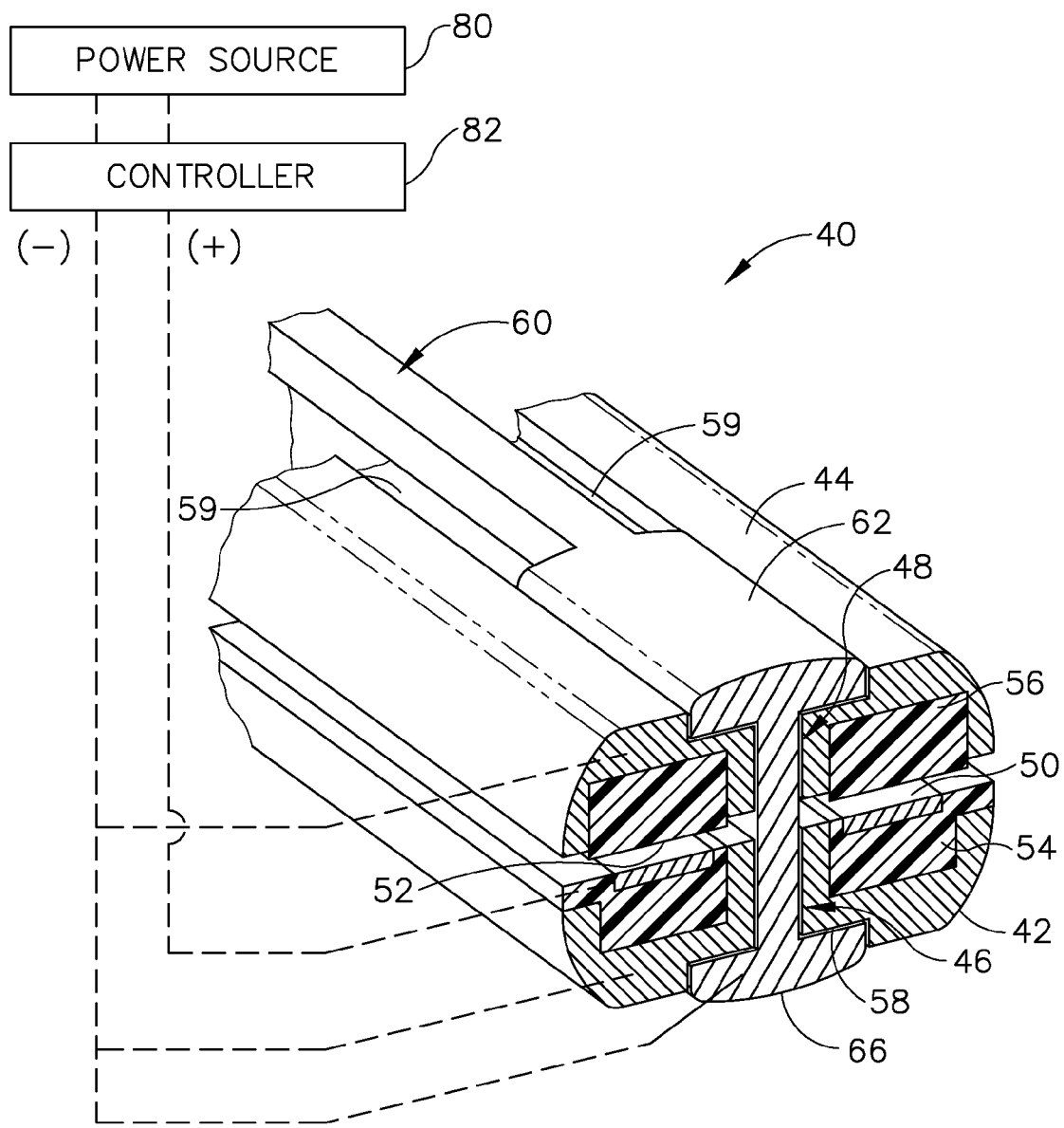
FIG. 4 depicts a cross-sectional end view of the end effector of FIG. 2 taken along the line 4-4 of FIG. 3, in a closed configuration and with the blade in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

As best seen in FIG. 4, the lower side of first jaw (42) includes a longitudinally extending recess (58) adjacent to slot (46); while the upper side of second jaw (44) includes a longitudinally extending recess (58) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze grip (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (42) when firing beam (60) is retracted to a proximal position and to hold jaw (42) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (44) toward jaw (44) when firing beam (60) is actuated distally by squeezing trigger (24) toward pistol grip (22).

With tissue layers captured between jaws (42, 44) firing beam (60) continues to advance distally by the user squeezing trigger (24) toward pistol grip (22). As firing beam (60) advances distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52).

While several of the teachings below are described as variations to electrosurgical instrument (10), it should be understood that various teachings below may also be incorporated into various other types of devices. By way of example only, in addition to being readily incorporated into electrosurgical instrument (10), various teachings below may be readily incorporated into the devices taught in any of the references cited herein, other types of electrosurgical devices, surgical staplers, surgical clip appliers, and tissue graspers, among various other devices. Other suitable devices into which the following teachings may be incorporated will be apparent to those of ordinary skill in the art in view of the teachings herein.

II. Exemplary Articulation Joint Configurations

Articulation section (36) of shaft (30) may take a variety of forms. By way of example only, articulation section (36) may be configured in accordance with one or more teachings of U.S. Pub. No. 2012/0078247, entitled "Articulation Joint Features for Articulating Surgical Device," published Mar. 29, 2012, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, the disclosure of which is incorporated by reference herein. Furthermore, articulation section may be configured in accordance with the teachings of at least one other of the references cited herein. Various other suitable forms that articulation section (36) may take will be apparent to those of ordinary skill in the art in view of the teachings herein.

III. Exemplary Articulation Control Configurations

As noted above, some versions of handpiece (20) include an articulation control (28), which is operable to control articulation section (36) of shaft (30) to thereby selectively position end effector (40) at various angles relative to the longitudinal axis defined by sheath (32). Several examples of forms that articulation control (28) and other components of handpiece (20) may take will be described in greater detail below, while further examples will be apparent to those of ordinary skill in the art in view of the teachings herein. By way of example only, some merely illustrative alternative examples of articulation control (28) are disclosed in U.S. Pub. No. 2012/0078243, entitled "Control Features for Articulating Surgical Device," published Mar. 29, 2012, the disclosure of which is incorporated by reference herein; and in U.S. Pub. No. 2012/0078244, entitled "Control Features for Articulating Surgical Device," published Mar. 29, 2012, the disclosure of which is incorporated by reference herein.

A. Exemplary Articulation Control with Perpendicular Rotary Knob

Figure 5:
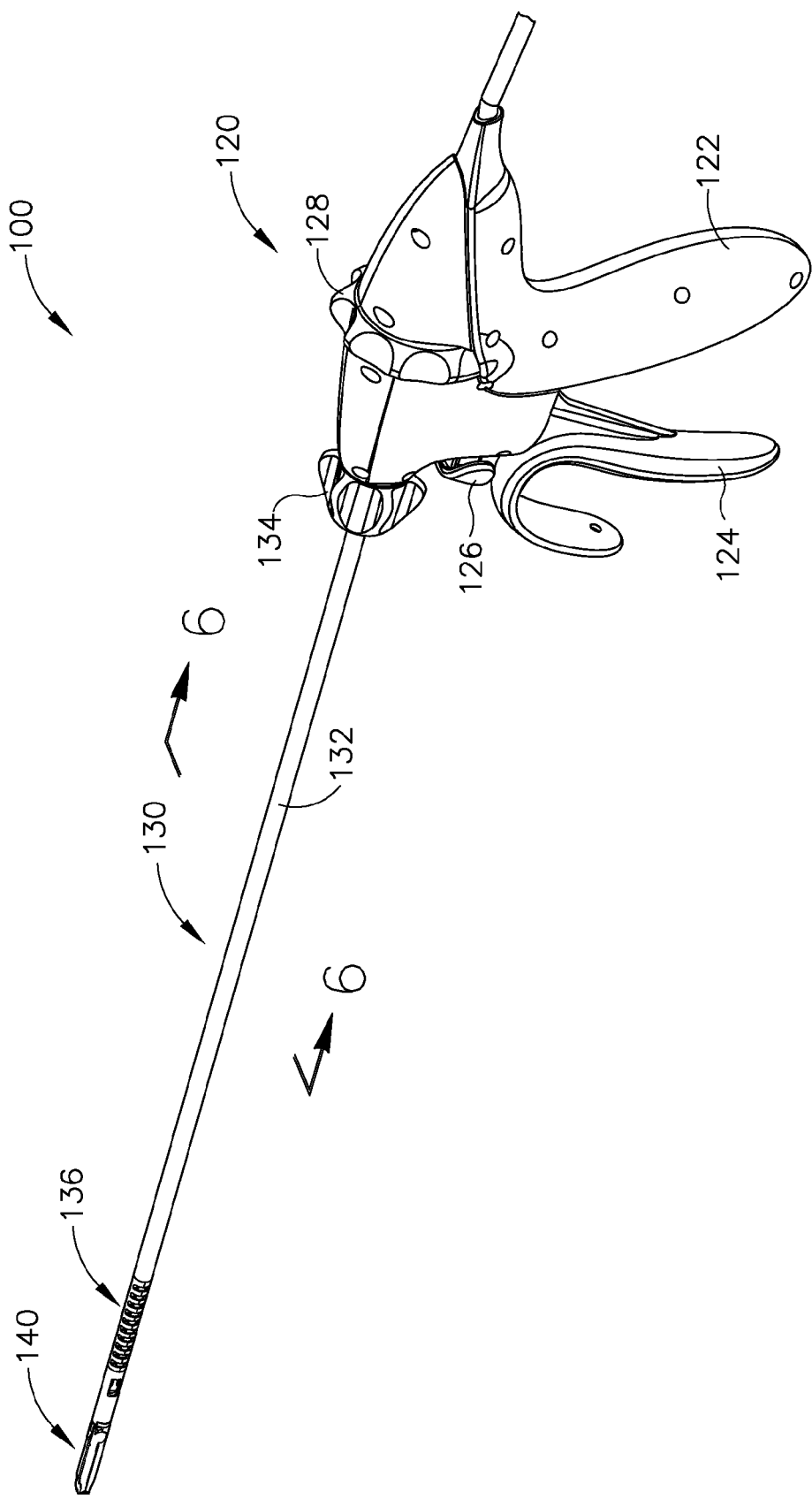
FIG. 5 depicts a perspective view of another exemplary electrosurgical medical device, with an articulation control knob.

FIG. 5 depicts an exemplary electrosurgical instrument (100) that includes a handpiece (120), a shaft (130) extending distally from handpiece (120), and an end effector (140) disposed at a distal end of shaft (130). Handpiece (120) of the present example includes a pistol grip (122), a pivoting trigger (124), an activation button (126), and a rotary articulation knob (128). Trigger (124) is pivotable toward and away from pistol grip (122) to selectively actuate end effector (140) as described above and as described in one or more reference cited herein. Activation button (126) is operable to selectively activate RF circuitry that is in communication with end effector (140), as also described above and as described in one or more of the references cited herein. In some versions, activation button (126) also serves as a mechanical lockout against trigger (124), such that trigger (124) cannot be fully actuated unless button (126) is being pressed simultaneously. Examples of how such a lockout may be provided are disclosed in one or more of the references cited herein. It should be understood that pistol grip (122), trigger (124), and button (126) may be modified, substituted, supplemented, etc. in any suitable way, and that the descriptions of such components herein are merely illustrative. Articulation knob (128) of the present example is operable to selectively control articulation section (136) of shaft (130), as will be described in greater detail below.

Shaft (130) of the present example includes an outer sheath (132), an articulation section (136) at the distal end of sheath (132), and a cutting member driver tube (138) that is slidably and coaxially disposed within sheath (132). Cutting member driver tube (138) is secured to a driver block (139), which is further secured to a cutting member (146) of end effector (140). Cutting member driver tube (138) is movable longitudinally to drive driver block (139) longitudinally, to thereby move cutting member (146) longitudinally. Cutting member (146) is essentially equivalent to firing beam (60) described above. The proximal portion (148) of end effector (140) includes an insert (not shown) that defines a channel containing the part of cutting member (146) that extends through proximal portion (148). This channel is configured to permit cutting member (146) to readily translate relative to the insert, while also preventing cutting member (146) from buckling within the insert when cutting member (146) encounters a load during distal advancement of cutting member (146).

Figure 13:
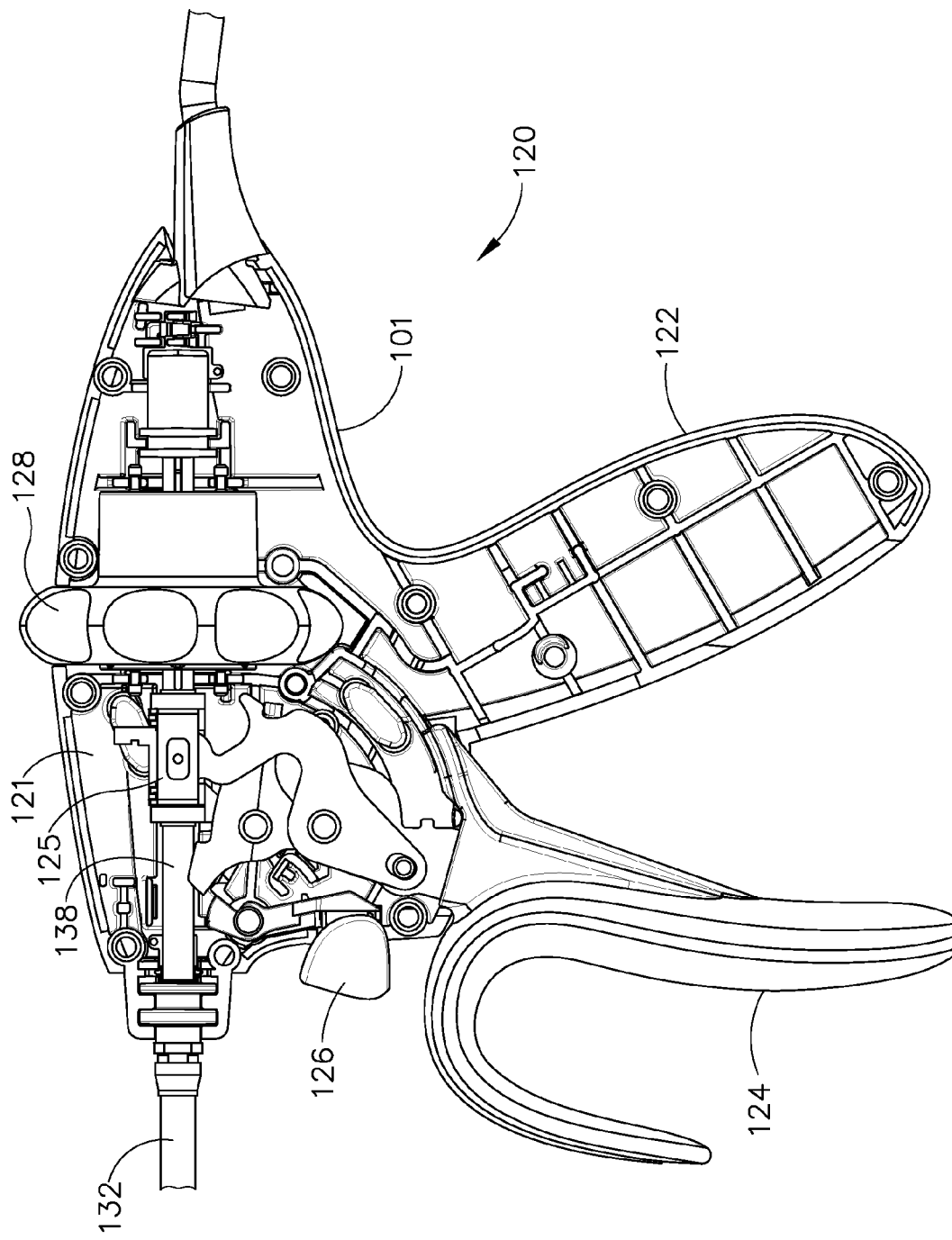
FIG. 13 depicts a side elevational view of the handle assembly of the device of FIG. 5, with a housing half removed.

In the present example, driver tube (138) is advanced distally by squeezing trigger (124) toward pistol grip (122); while driver tube (138) is retracted proximally by releasing trigger (124) and/or by actively moving trigger (124) away from pistol grip (122). As shown in FIG. 13, a yoke (125) couples trigger (124) with driver tube (138). Of course, cutting member (146) may be moved in any other suitable fashion. Articulation section (136) of the present example is operable to selectively position end effector (140) at various angles relative to the longitudinal axis defined by sheath (132). Various examples of forms that articulation section (136) and other components of shaft (130) may take are described in various references cited herein, while further examples will be apparent to those of ordinary skill in the art in view of the teachings herein. Similarly, end effector (140) may be configured in accordance with end effector (40) described above, in accordance with the teachings of various references cited herein, and/or in any other suitable way as will be apparent to those of ordinary skill in the art in view of the teachings herein.

In some versions, shaft (130) is also rotatable about the longitudinal axis defined by sheath (132), relative to handpiece (120), via a knob (134). Such rotation may provide rotation of end effector (140) and shaft (130) unitarily. In some other versions, knob (134) is operable to rotate end effector (140) without rotating any portion of shaft (130) that is proximal of articulation section (136). As another merely illustrative example, electrosurgical instrument (100) may include one rotation control that provides rotatability of shaft (130) and end effector (140) as a single unit; and another rotation control that provides rotatability of end effector (140) without rotating any portion of shaft (130) that is proximal of section (136). Other suitable rotation schemes will be apparent to those of ordinary skill in the art in view of the teachings herein. Of course, rotatable features may simply be omitted if desired. In any versions of a device that provide rotation of a shaft (130) and/or end effector (140), a rotation knob (134) and/or shaft (130) and/or end effector (140) may include one or more markings facilitating visual identification of the rotational position. For instance, a user may correlate a marking on a rotation knob (134) with a corresponding marking on a shaft (130) and/or end effector (140) to better understand the orientation of such components with respect to the patient and instrument (100).

Figure 6:
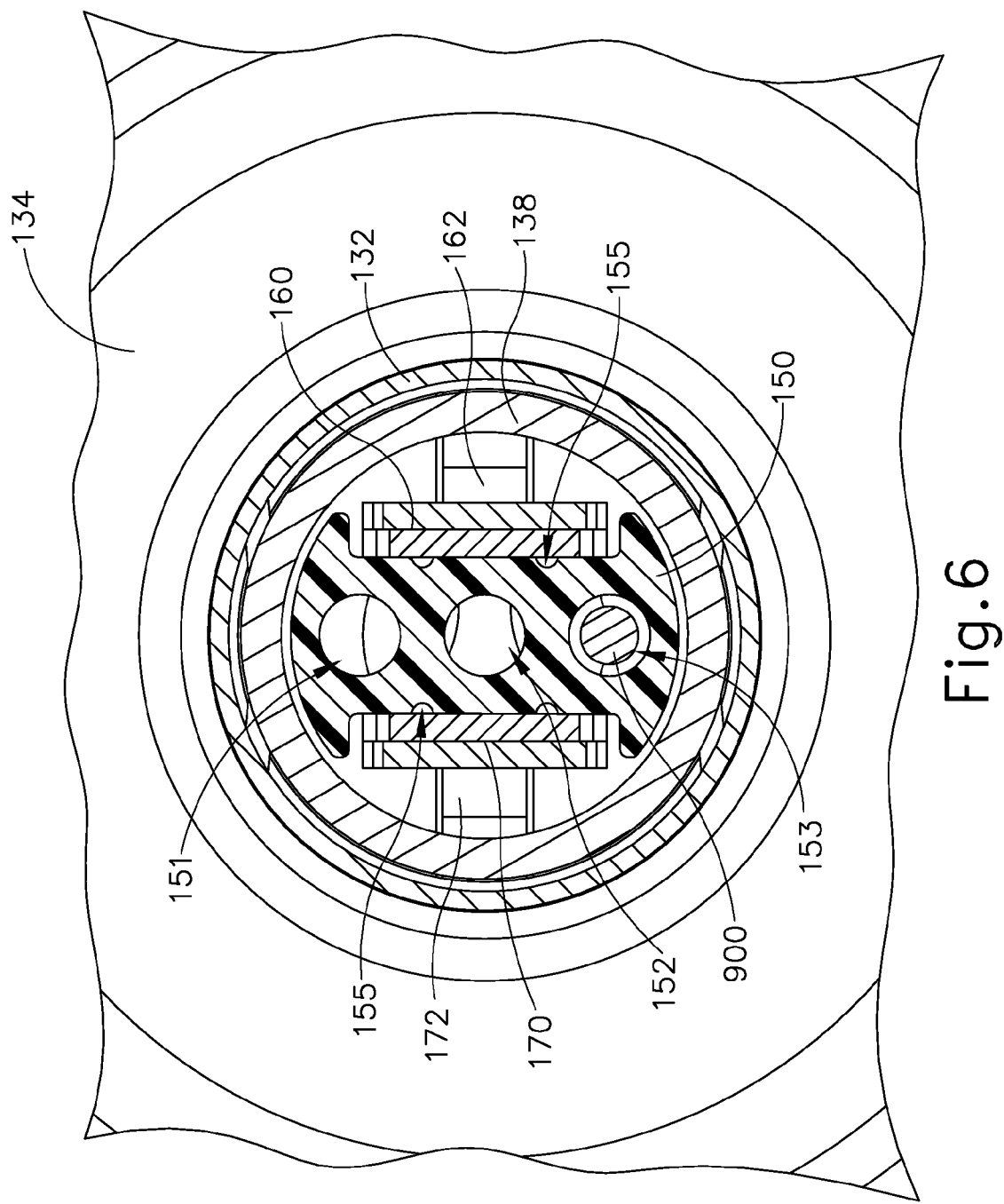
FIG. 6 depicts a cross-sectional end view of a shaft assembly of the device of FIG. 5, taken along line 6-6 of FIG. 5.

FIGS. 6-12 show various components of shaft (130) that provide control for articulation of articulation section (136). In particular, these components include a separator (150), a first articulation band (160) with an associated drive member (162), and a second articulation band (170) with an associated drive member (172). As best seen in FIG. 6, separator (150) includes an upper lumen (151), a middle lumen (152), and a lower lumen (153). Separator (150) also includes side recesses (154), a distal projection (156), and a gap (158). Separator (150) is disposed within cutting member driver tube (138) and maintains a fixed longitudinal position during operation of instrument (100). Thus, separator (150) and outer sheath (132) remain stationary relative to each other and relative to handpiece (120); while cutting member driver tube (138) reciprocates relative to separator (150), outer sheath (132), and handpiece (120). Distal projection (156) is configured to permit translation of driver block (139) substantially free from interference by distal projection (156) or by any other portion of separator (150).

In the present example, separator (150) is formed as two pieces arranged in an end-to-end configuration, with a distal projection from the proximal piece helping to define gap (158). Of course, separator (150) may alternatively be formed as a single piece or any other suitable number of pieces. By way of example only, gap (158) may be formed as a cutout from a single piece of material.

As will be described in greater detail below, a wire (900) extends through separator (150) to provide electrical communication to end effector (140). In particular, wire (900) extends through middle lumen (152) from the proximal end of separator (150) until wire (900) reaches gap (158). At gap (158), wire (900) transitions down to lower lumen (153), and extends through lower lumen (153) until reaching the distal end of separator (150). Wire (900) then extends across articulation section (136) to end effector (140). Wire (900) is thus operable to communicate power from a power source to end effector (140) in accordance with the teachings herein and in accordance with the teachings of various references cited herein. Distal projection (156) protects wire (900) from driver block (139), such that driver block (139) is unable to contact wire (900) regardless of the longitudinal position of driver block (139) along distal projection (156).

Figure 7:
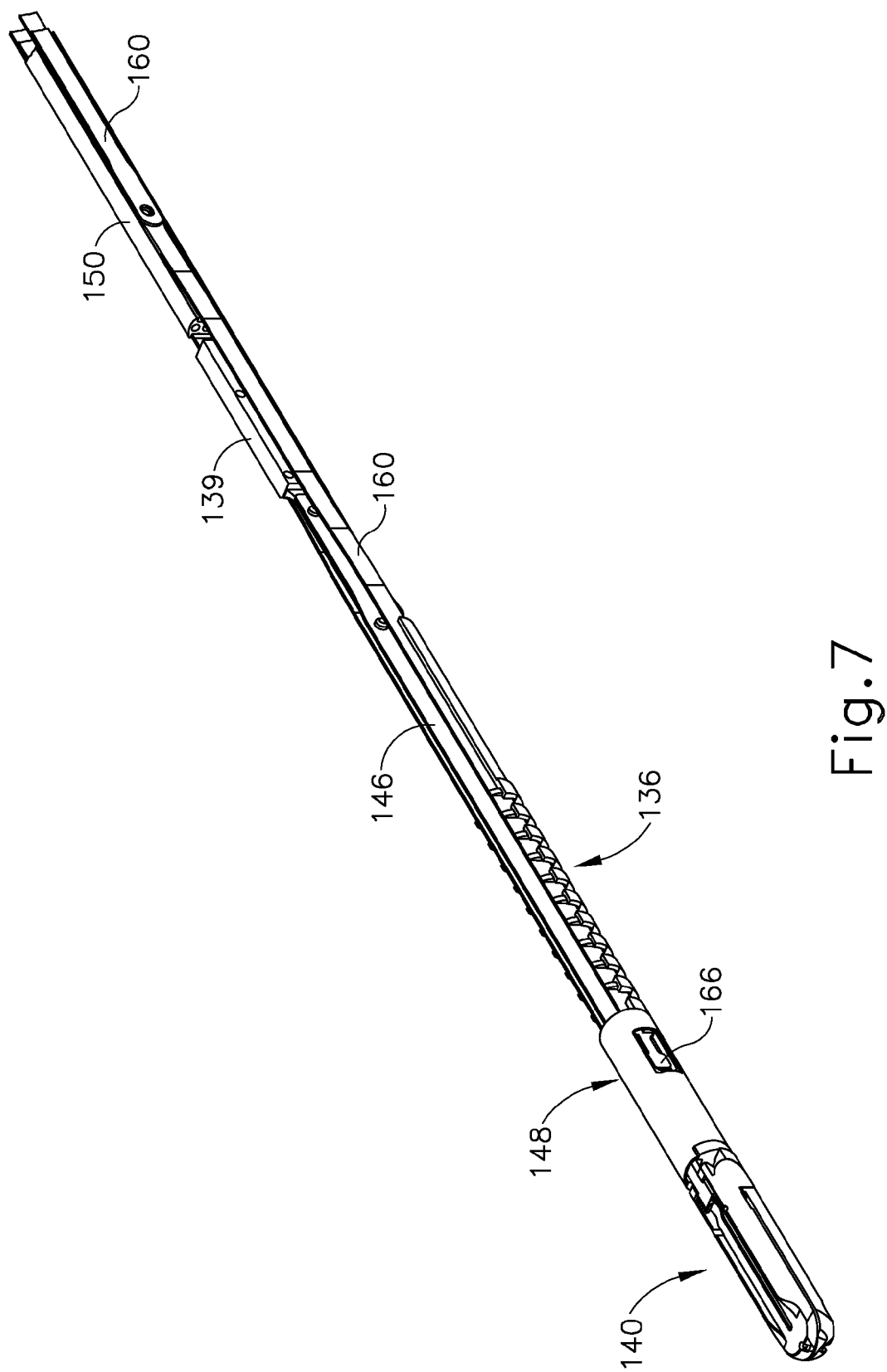
FIG. 7 depicts a perspective view of components of the shaft assembly and end effector of the device of FIG. 5.
Figure 8:
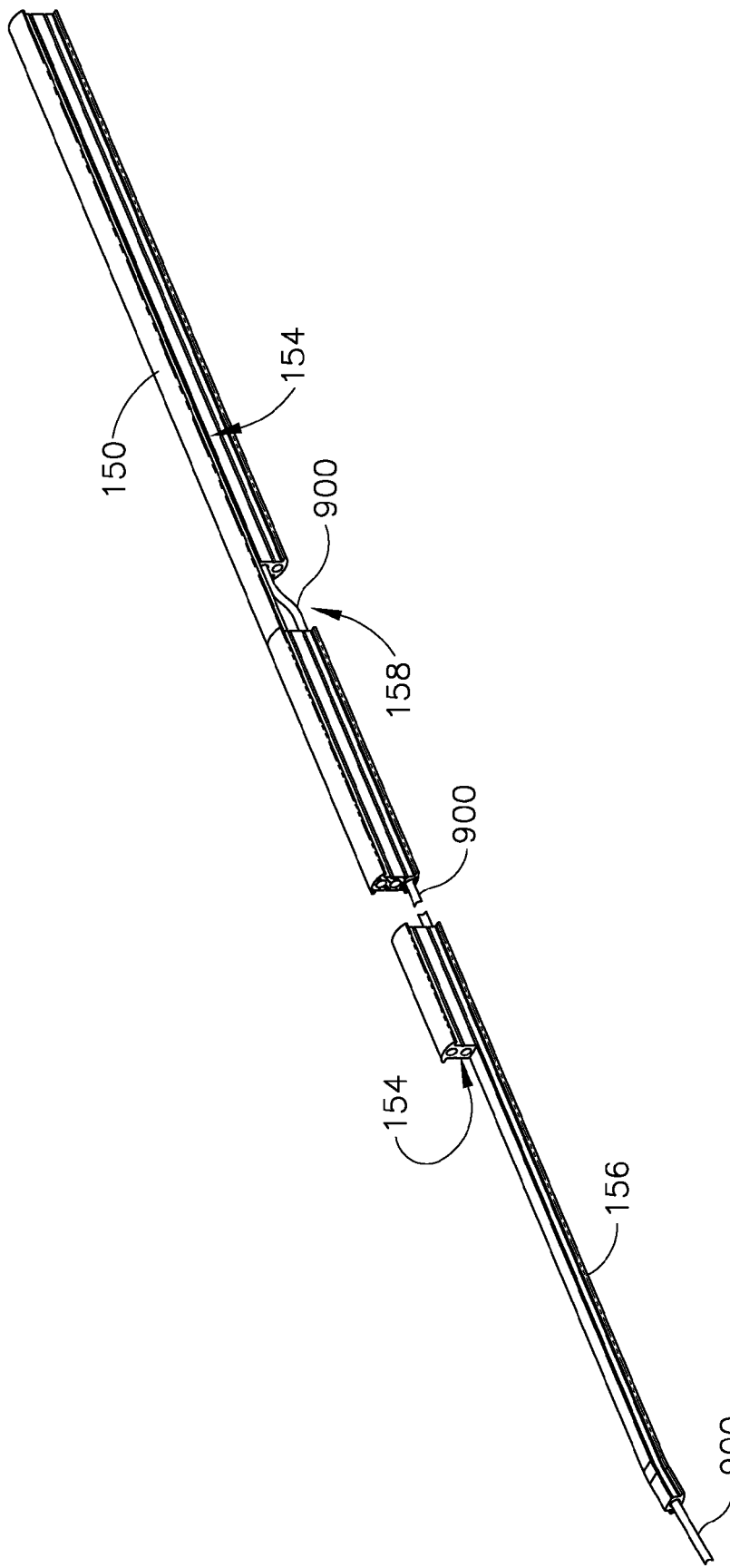
FIG. 8 depicts a perspective view of a support member of the shaft assembly of the device of FIG. 5.

First articulation band (160) is slidably disposed in one side recess (154) of separator (150) while second articulation band (170) is slidably disposed in the other side recess (154) of separator (150). Referring back to FIG. 6, side recesses (154) include longitudinally extending grooves (155) that are configured to reduce the contact surface area with articulation bands (160, 170), thereby reducing friction between separator (150) and articulation bands (160, 170). Separator (150) may also be formed of a low friction material and/or include a surface treatment to reduce friction. Articulation bands (160, 170) both extend longitudinally along the entire length of shaft (130), including through articulation section (136). As shown in FIG. 7, the distal end (166) of first articulation band (160) is secured to one side of the proximal portion (148) of end effector (140) at an anchor point. The distal end (176) of second articulation band (170) is secured to the other side of proximal portion (148) of end effector (140) at an anchor point. As will be described in greater detail below, rotary articulation knob (128) is operable to selectively advance one articulation band (160, 170) distally while simultaneously retracting the other articulation band (160, 170) proximally, and vice-versa. It should be understood that this opposing translation will cause articulation section (136) to bend, thereby articulating end effector (140). In particular, end effector (140) will deflect toward whichever articulation band (160, 170) is being retracted proximally; and away from whichever articulation band (160, 170) is being advanced distally.

Figure 9:
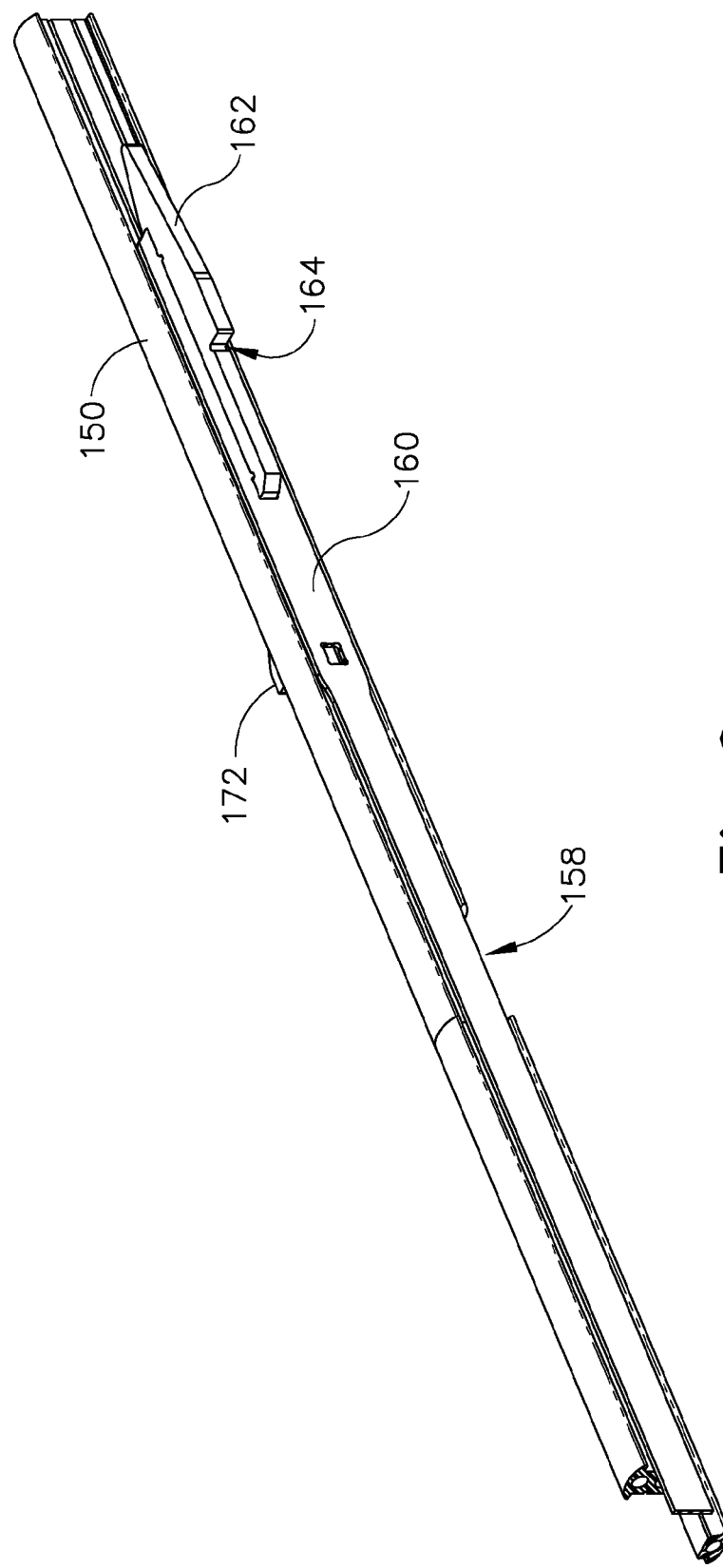
FIG. 9 depicts a partial perspective view of articulation control components of the device of FIG. 5, along one side of the support member.
Figure 10:
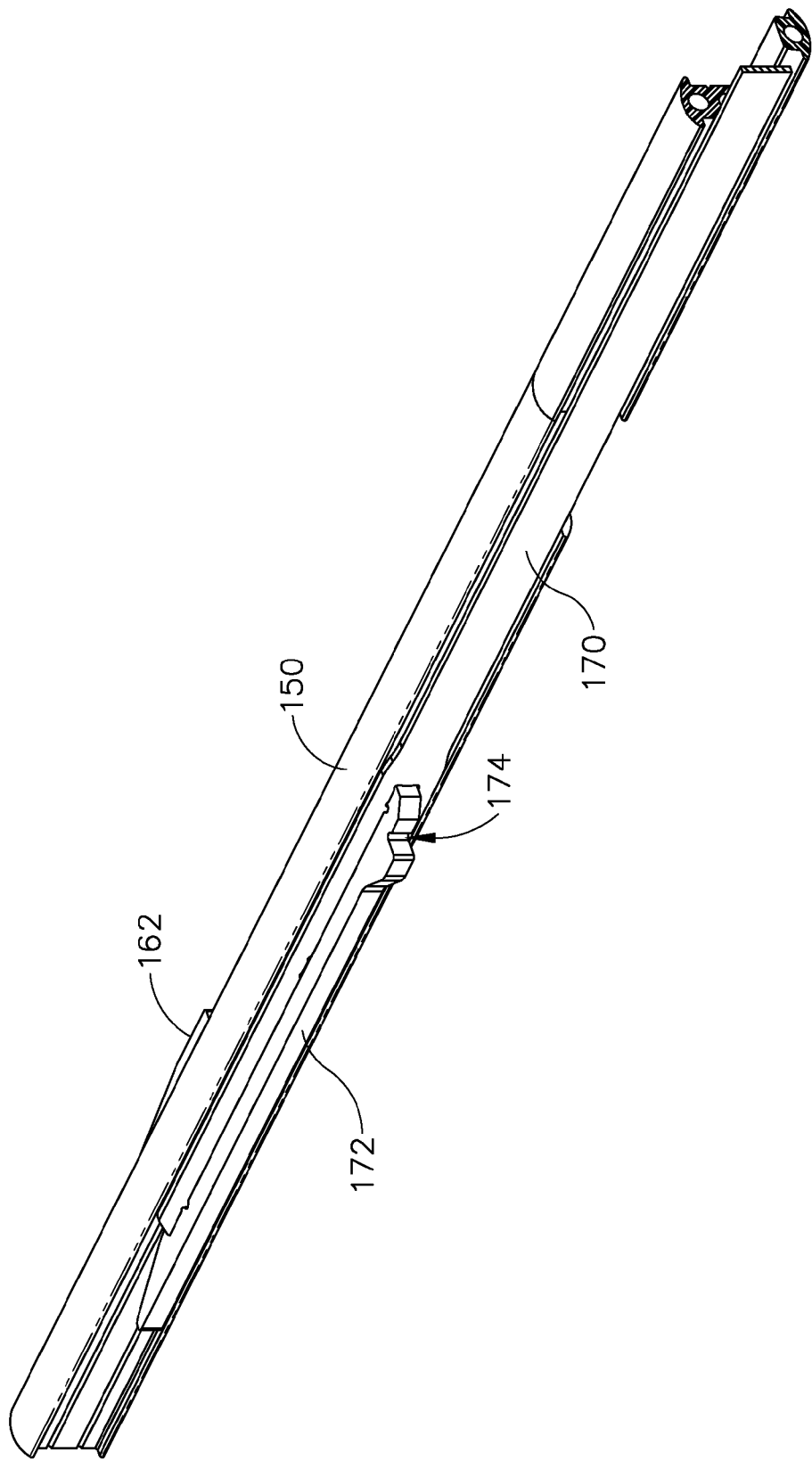
FIG. 10 depicts a partial perspective view of articulation control components of the device of FIG. 5, along another side of the support member.
Figure 11:
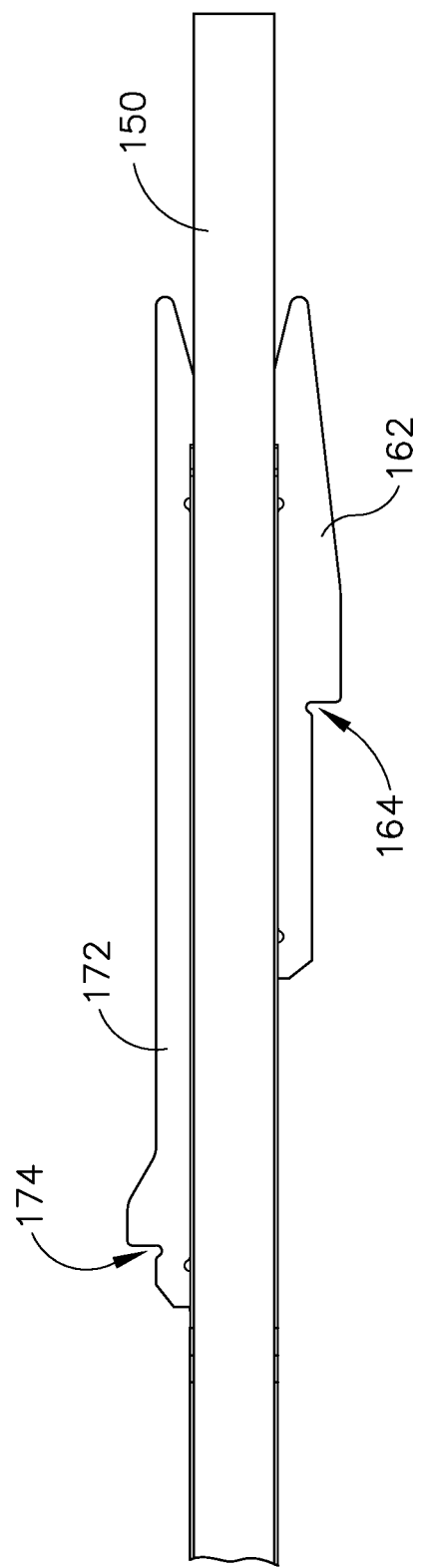
FIG. 11 depicts a top plan view of the articulation control components of FIGS. 9-10.
Figure 12:
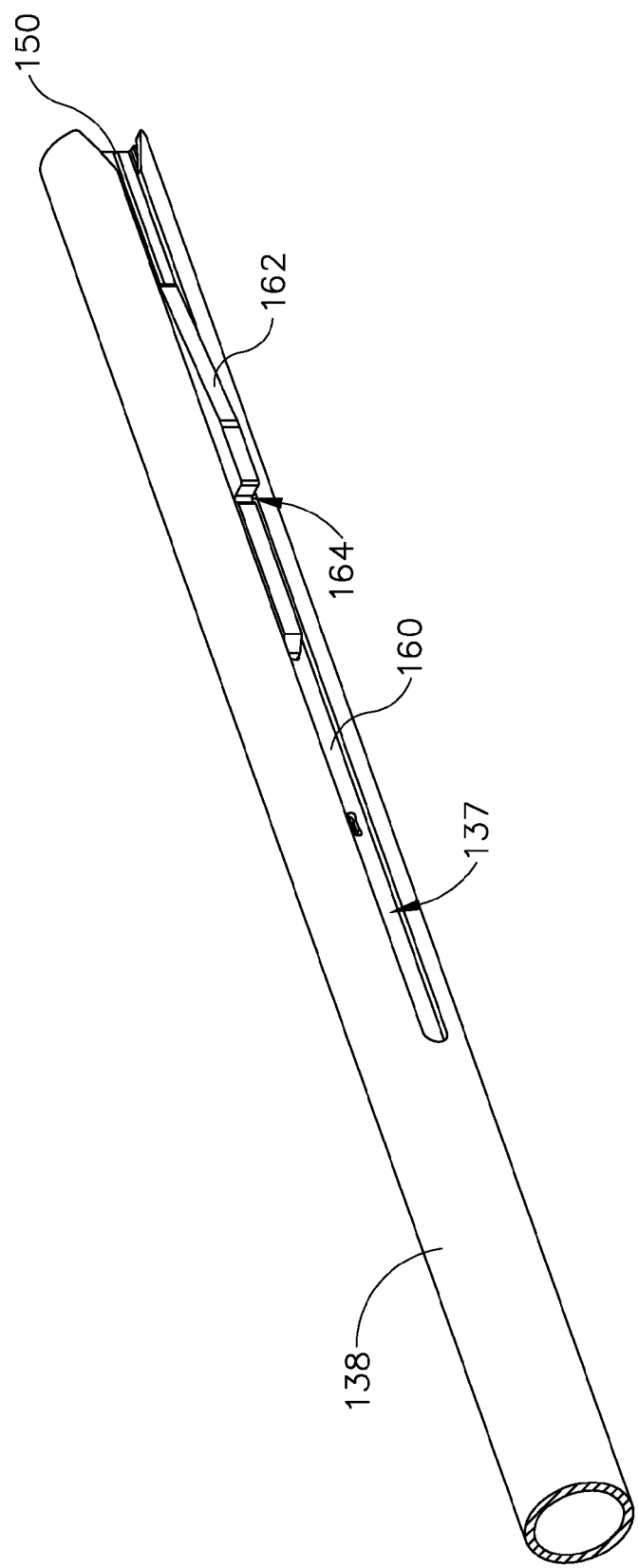
FIG. 12 depicts a partial perspective view of the articulation control components of FIG. 9 surrounded by a sheath.

As best seen in FIG. 9, drive member (162) is unitarily secured to articulation band (160) and includes a notch (164)

extending laterally inwardly. As best seen in FIG. 10, drive member (172) is unitarily secured to articulation band (170) and includes a notch (174) extending laterally inwardly. As best seen in FIG. 11, drive members (162, 164) are spaced and configured such that notches (164, 174) are at different longitudinal positions along the length of separator (150). As best seen in FIG. 12, the proximal portion of cutting member driver tube (138) includes longitudinally extending slots (137). Drive members (162, 172) are slidably disposed in slots (137) and notches (164, 174) are radially positioned outside the outer circumference of cutting member driver tube (138). Slots (137) are configured to enable free translation of cutting member driver tube (138) relative to drive members (162, 172), to thus enable free actuation of cutting member (164) regardless of the articulation state of articulation section (136). In other words, slots (137) are configured to enable free translation of drive members (162, 172) relative to cutting member driver tube (138), to thus enable free articulation of articulation section (136) regardless of the longitudinal position of cutting member (164).

Figure 14:
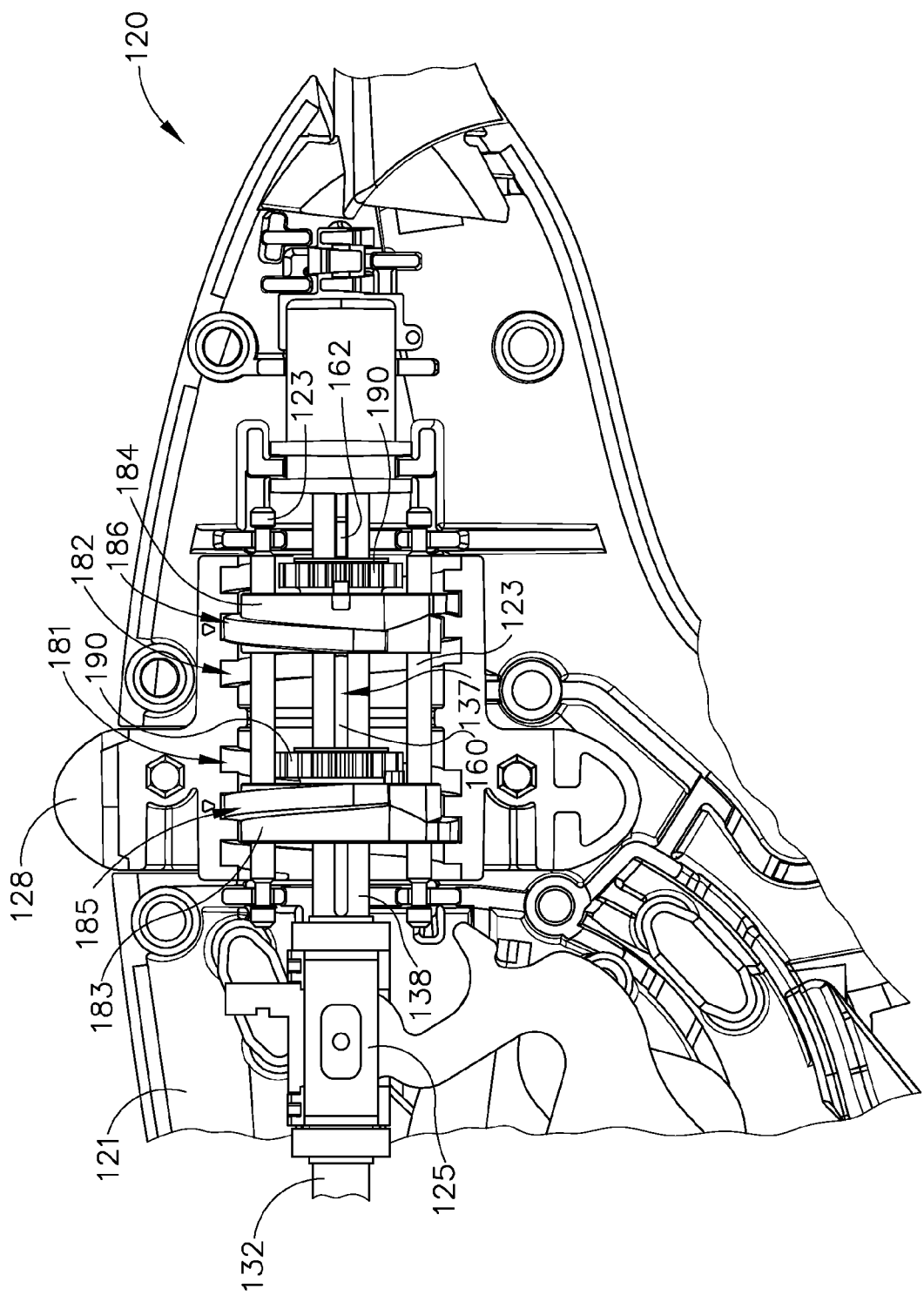
FIG. 14 depicts a side elevational view of articulation control components of the handle assembly of FIG. 13, with half of an articulation control knob body removed.

As shown in FIGS. 13-14, rotary articulation knob (128) is coaxially positioned about the proximal portion of driver tube (138) and encompasses drive members (162, 172). Articulation knob (128) is oriented perpendicular to the longitudinal axis defined by shaft (130) and is rotatable about the longitudinal axis defined by shaft (130). As will be described in greater detail below, such rotation of articulation knob (128) will cause opposing translation of drive members (162, 172), with the directions of such opposing translations depending on the direction in which articulation knob (128) is rotated, such that rotation of articulation knob (128) will articulate end effector (140). As shown in FIG. 14, articulation knob (128) includes a first internal threading (180) and a second internal threading (182). Threadings (181, 182) have opposing pitch angles or orientations in this example.

Figure 15:
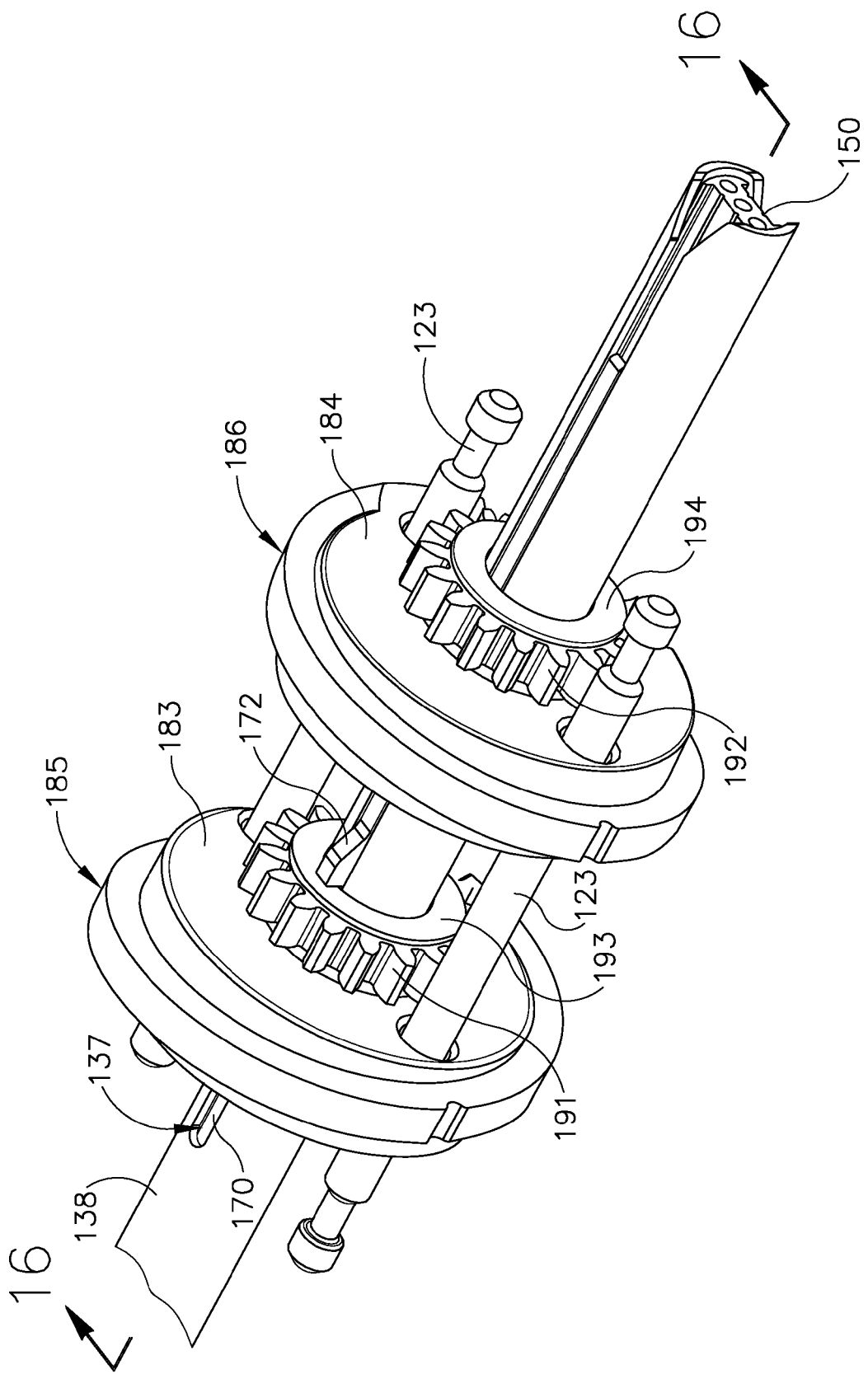
FIG. 15 depicts a perspective view of articulation control components of the handle assembly of FIG. 13, coupled with the articulation control components of FIGS. 9-10.

As best seen in FIGS. 14-15, a first lead screw (183) and a second lead screw (184) are slidably disposed along a pair of pins (123), which are secured to housing (121). Thus, lead screws (183, 184) are operable to translate within housing (121) but are prevented from rotating within housing (121). First lead screw (183) includes exterior threading (185) that is engaged with threading (181) of articulation knob (128); while second lead screw (184) includes exterior threading (186) that is engaged with threading (182) of articulation knob (128). The pitch angle of threading (185) complements the pitch angle of threading (181); while the pitch angle of threading (186) complements the pitch angle of threading (182). It should therefore be understood that, due to the opposing pitch angles, rotation of knob (128) in a first direction will drive lead screw (183) distally while simultaneously driving lead screw (184) proximally; and rotation of knob in a second direction will drive lead screw (183) proximally while simultaneously driving lead screw (184) distally.

The angles of threading (181, 182, 185, 186) are also configured such that articulation section (136) will be effectively locked in any given articulated position, such that transverse loads on end effector (140) will generally not bend articulation section (136), due to friction between threading (181, 182, 185, 186). In other words, articulation section (136) will only change its configuration when knob (128) is rotated. While the angles of threading may substantially prevent bending of articulation section (136) in response to transverse loads on end effector (140), the angles may still provide ready rotation of articulation knob (128) to translate lead screws (183, 184). By way of example only, the angles of threading (181, 182, 185, 186) may be approximately +/−2 degrees or approximately +/−3 degrees. Other suitable angles will be apparent to those of ordinary skill in the art in view of the teachings herein. It should also be understood that threading (181, 182, 185, 186) may have a square or rectangular cross-section or any other suitable configuration.

Figure 16:
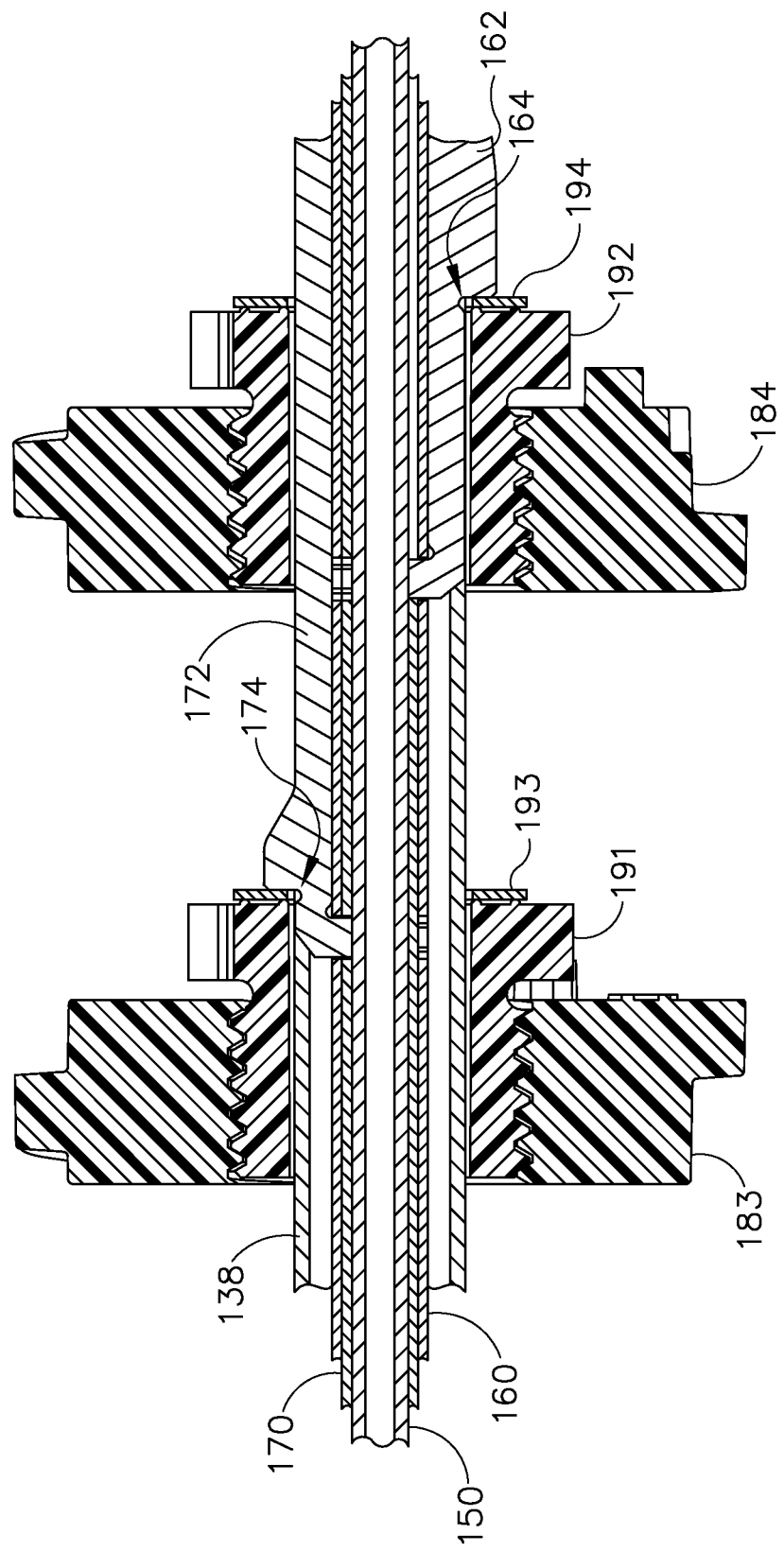
FIG. 16 depicts a side cross-sectional view of the articulation control components of FIG. 15, taken along line 16-16 of FIG. 15.

As best seen in FIGS. 15-16, a first tensioner gear (191) is threadably engaged with first lead screw (183); while a second tensioner gear (192) is threadably engaged with second lead screw (184). Thus, the longitudinal position of first tensioner gear (191) relative to first lead screw (183) may be adjusted by rotating first tensioner gear (191) relative to first lead screw (183); while the longitudinal position of second tensioner gear (192) relative to second lead screw (184) may be adjusted by rotating second tensioner gear (192) relative to second lead screw (184). Otherwise, first tensioner gear (191) will translate unitarily with first lead screw (183); while second tensioner gear (192) will translate unitarily with second lead screw (184).

First tensioner gear (191) is also engaged with a washer (193), which is further engaged with notch (174) of drive member (172). The engagement between washer (193) and drive member (172) is such that washer (193) and drive member (172) will translate together. In some versions, washer (193) is secured to tensioner gear (191) in such a manner that tensioner gear (191) both pulls washer (193) distally and pushes washer (193) proximally. Thus, in some such versions, first lead screw (183) is operable to both push articulation band (170) distally and pull articulation band (170) proximally, depending on which direction knob (128) is rotated. In the present example, however, tensioner gear (191) merely abuts washer (193), such that tensioner gear (191) is operable to push washer (193) proximally but cannot pull washer (193) distally. Thus, in the present example, first lead screw (183) is operable to pull articulation band (170) proximally but cannot actively push articulation band (170) distally. Instead, first lead screw (183) may simply pull tensioner gear (191) distally to enable articulation band (170), drive member (172), and washer (193) to be driven distally in response to proximal retraction of articulation band (160) as communicated through articulation section (136). Other suitable relationships will be apparent to those of ordinary skill in the art in view of the teachings herein. It should also be understood that drive member (172) and/or washer (193) may be rotatable relative to tensioner gear (191), which may permit rotation of shaft (130) by knob (134). As described in greater detail below, tensioner gear (191) may be used to take out any tolerance gaps between drive member (172) and lead screw (183).

Similarly, second tensioner gear (192) is engaged with a washer (194), which is further engaged with notch (164) of drive member (162). The engagement between washer (194) and drive member (162) is such that washer (194) and drive member (162) will translate together. In some versions, washer (194) is secured to tensioner gear (192) in such a manner that tensioner gear (192) both pulls washer (194) distally and pushes washer (194) proximally. Thus, in some such versions, second lead screw (184) is operable to both push articulation band (160) distally and pull articulation band (160) proximally, depending on which direction knob (128) is rotated. In the present example however, tensioner gear (192) merely abuts washer (194), such that tensioner gear (192) is operable to push washer (194) proximally but cannot pull washer (194) distally. Thus, in the present example, second lead screw (184) is operable to pull articulation band (160) proximally but cannot actively push articulation band (160) distally. Instead, second lead screw (184) may simply pull tensioner gear (192) distally to enable articulation band (160), drive member (162), and washer (194) to be driven distally in response to proximal retraction of articulation band (170) as communicated through articulation section (136). Other suitable relationships will be apparent to those of ordinary skill in the art in view of the teachings herein. It should also be understood that drive member (162) and/or washer (194) may be rotatable relative to tensioner gear (192), which may permit rotation of shaft (130) by knob (134). As described in greater detail below, tensioner gear (192) may be used to take out any tolerance gaps between drive member (162) and lead screw (184).

Figure 17A:
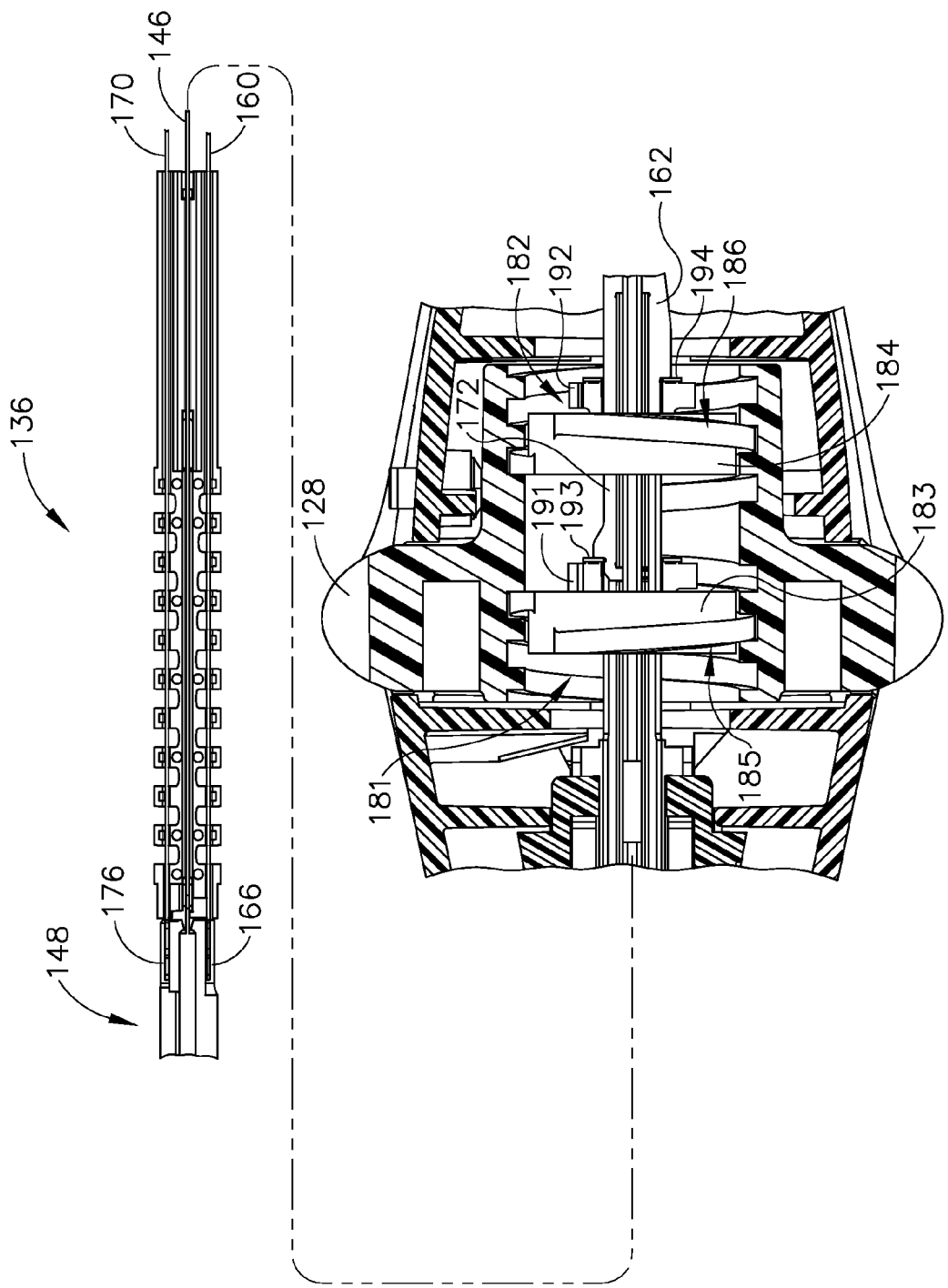
FIG. 17A depicts a partial cross-sectional view of articulation control components and the articulation section of the shaft of the device of FIG. 5, with the articulation section in a substantially straight configuration.
Figure 17B:
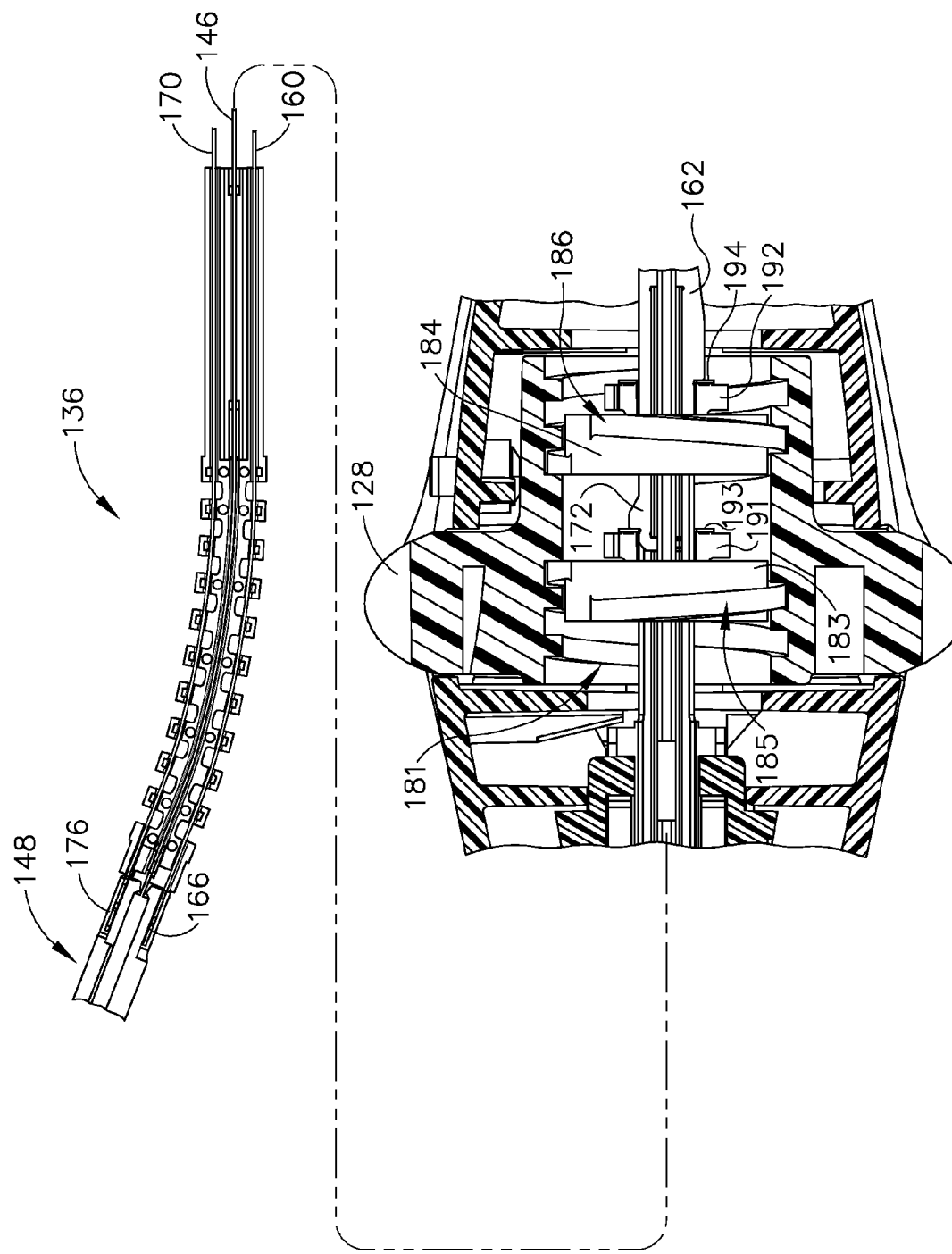
FIG. 17B depicts a partial cross-sectional view of the components of FIG. 17A, with the articulation section in a first stage of articulation.
Figure 17C:
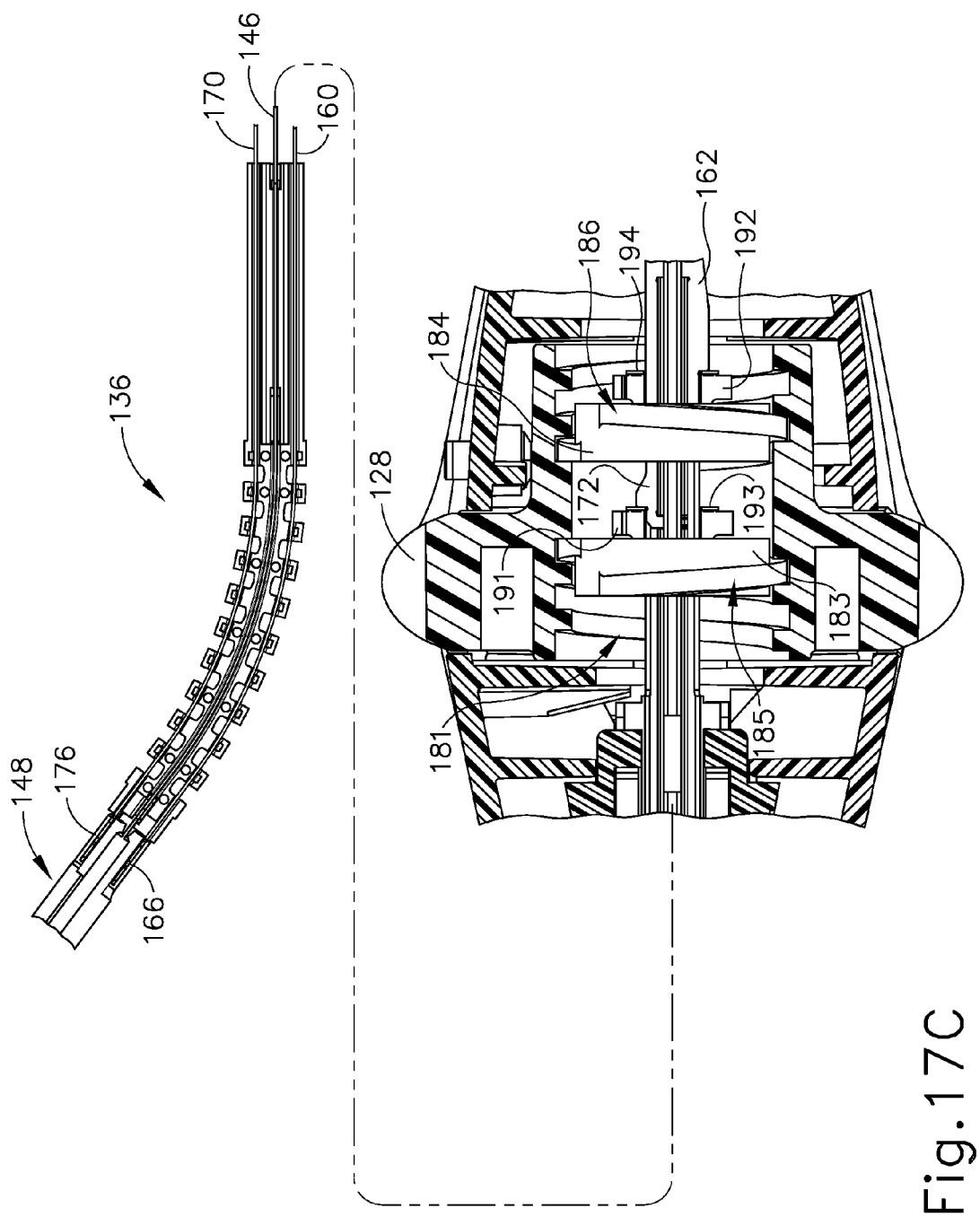
FIG. 17C depicts a partial cross-sectional view of the components of FIG. 17A, with the articulation section in a second stage of articulation.

FIGS. 17A-17C show several of the above described components interacting to bend articulation section (136) to articulate end effector (140). In FIG. 17A, articulation (136) is in a substantially straight configuration. Then, knob (128) is rotated, which causes lead screw (183) to translate proximally and lead screw (184) to advance distally. This proximal translation of lead screw (183) pulls articulation band (170) proximally, which causes articulation section (136) to start bending as shown in FIG. 17B. This bending of articulation section (136) pulls articulation band (160) distally. The distal advancement of lead screw (184) in response to rotation of knob (128) enables articulation band (160) and drive member (162) to advance distally. In some other versions, the distal advancement of lead screw (184) actively drives drive member (162) and articulation band (160) distally. As the user continues rotating knob (128), the above described interactions continue in the same fashion, resulting in further bending of articulation section (136) as shown in FIG. 17C. It should be understand that rotating knob (128) in the opposite direction will cause articulation section (136) to straighten, and further rotation in the opposite direction will cause articulation section (136) to bend in the opposite direction.

In some versions, knob (128) includes a visual indicator that is associated with articulation section (136) being in a substantially straight configuration. Such a visual indicator may align with a corresponding visual indicator on housing (121) of handpiece (120). Thus, when a user has rotated knob (128) to make articulation section (136) approach a substantially straight configuration, the user may observe such indicators to confirm whether articulation section (136) has in fact reached a substantially straight configuration. By way of example only, this may be done right before instrument (100) is withdrawn from a trocar to reduce the likelihood of articulation section (136) snagging on a distal edge of the trocar. Of course, such indicators are merely optional.

In some instances, manufacturing inconsistencies may result in articulation bands (160, 170) having slightly different lengths. In addition or in the alternative, there may be inherent manufacturing related inconsistencies in the initial positioning of lead screws (183, 184) relative to articulation knob (128), inconsistencies in the initial positioning of tensioner gears (191, 192) relative to lead screws (183, 184), and/or other inconsistencies that might result in undesirable positioning/relationships of articulation bands (160, 170). Such inconsistencies may result in lost motion or slop in the operation of the articulation features of instrument (100). To address such issues, tensioner gears (191, 192) may be rotated relative to lead screws (183, 184) to adjust the longitudinal position of drive members (162, 172) relative to lead screws (183, 184). For instance, if there is insufficient tension in articulation band (170), tensioner gear (191) may be rotated to drive washer (193) and drive member (172) proximally until articulation band (170) reaches a sufficient degree of tension. Similarly, if there is insufficient tension in articulation band (160), tensioner gear (192) may be rotated to drive washer (195) and drive member (162) proximally until articulation band (160) reaches a sufficient degree of tension. Lead screws (183, 184) may remain substantially stationary during such adjustments. Articulation section (136) may remain substantially straight during such adjustments and may even be held substantially straight during such adjustments.

In some versions, tensioner gears (191, 192) are rotated manually. In some other versions, tensioner gears (191, 192) are rotated automatically by a rack or other gear. In some such automated calibration systems, a control logic may monitor the load on a motor that is being used to drive a calibrating rack or gear that is engaged with tensioner gear (191, 192), and may automatically stop driving such a rack or gear when the load reaches a threshold associated with proper tensioning of band (160, 170). For instance, in cases where manufacturing inconsistencies or tolerance provide an initial gap between tensioner gears (191, 192) and washers (193, 194), or between washers (193, 194) and drive members (162, 172), tensioner gears (191, 192) may be rotated until such gaps are closed and sufficient contact is made between previously gapped components. As another merely illustrative variation, tensioner gears (191, 192) may be automatically stopped when the proximal ends of bands (160, 170) and/or drive members (162, 172) reach a certain point. Various suitable ways in which tensioner gears (191, 192) may be adjusted will be apparent to those of ordinary skill in the art in view of the teachings herein. It should also be understood that tensioner gears (191, 192) may be heat staked, glued, welded, or otherwise bonded to the respective lead screws (183, 184) when the gaps between drive members (162, 172) and their respective washers (193, 194) reach zero. Such bonding may prevent subsequent movement of tensioner gears (191, 192) relative to their respective lead screws (183, 184).

As another merely illustrative example, manufacturing inconsistencies may be addressed at the distal ends of bands (160, 170). For instance, before the distal ends of bands (160, 170) are secured to the proximal portion (148) of end effector (140), articulation section (136) may be held in a straight configuration and bands (160, 170) may be pulled distally to remove any slack in bands (160, 170). With bands (160, 170) both being in tension, bands (160, 170) may then be welded or otherwise secured to proximal portion (148) of end effector (140). It should be understood that this form of calibration is not limited to instrument (100), such that this form of calibration may be readily applied to various other instruments described herein, among others. Other suitable structures and methods for calibration will be apparent to those of ordinary skill in the art in view of the teachings herein.

IV. Other Exemplary Features

It should be understood that any of the versions of electrosurgical instrument (10) described herein may include various other features in addition to or in lieu of those described above. Several examples of such other features are described below, while other features will be apparent to those of ordinary skill in the art in view of the teachings herein.

A. Exemplary Alternative Firing Assembly

Figure 18:
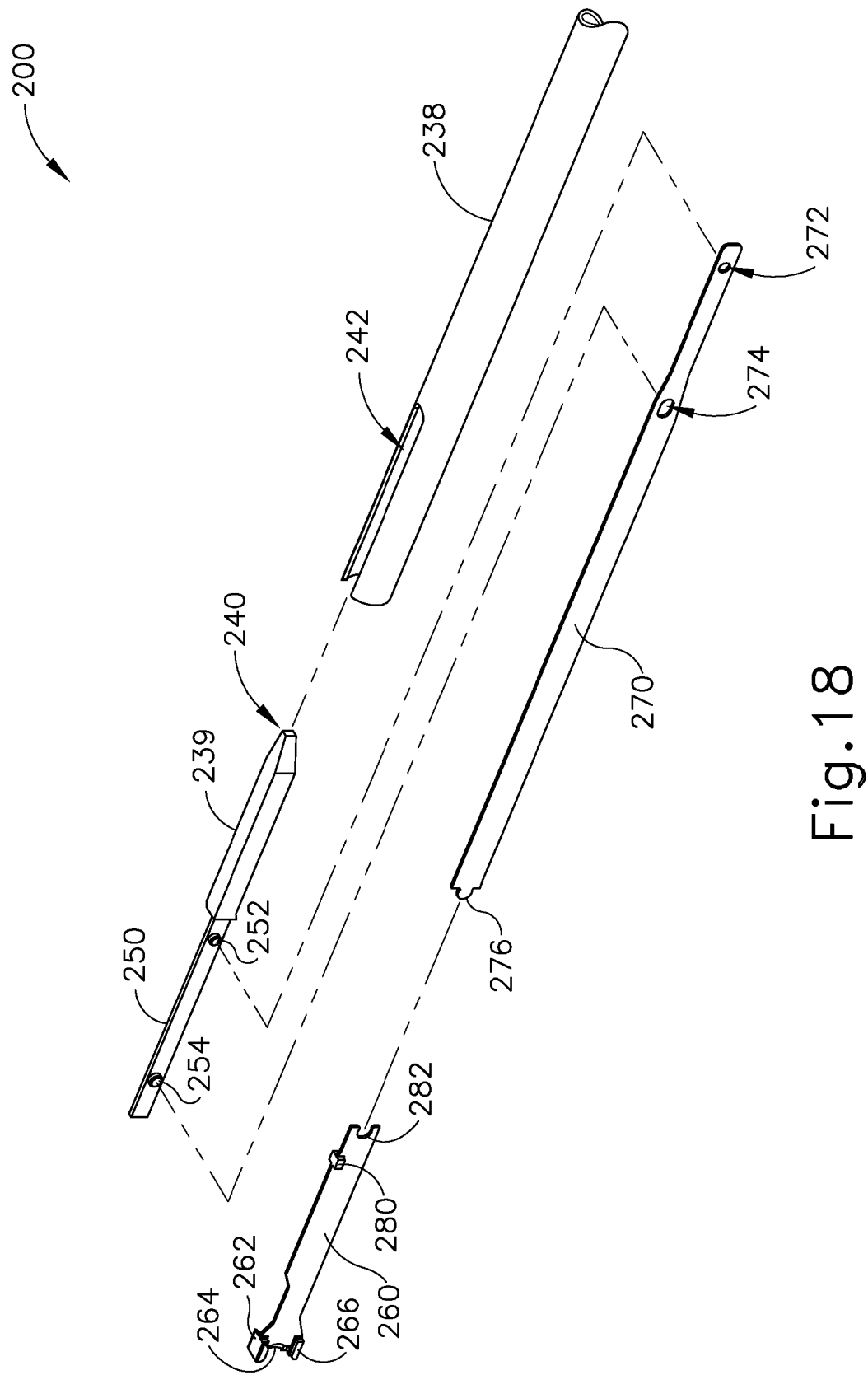
FIG. 18 depicts an exploded perspective view of an exemplary firing beam assembly suited for incorporation in the device of FIG. 5.
Figure 19:
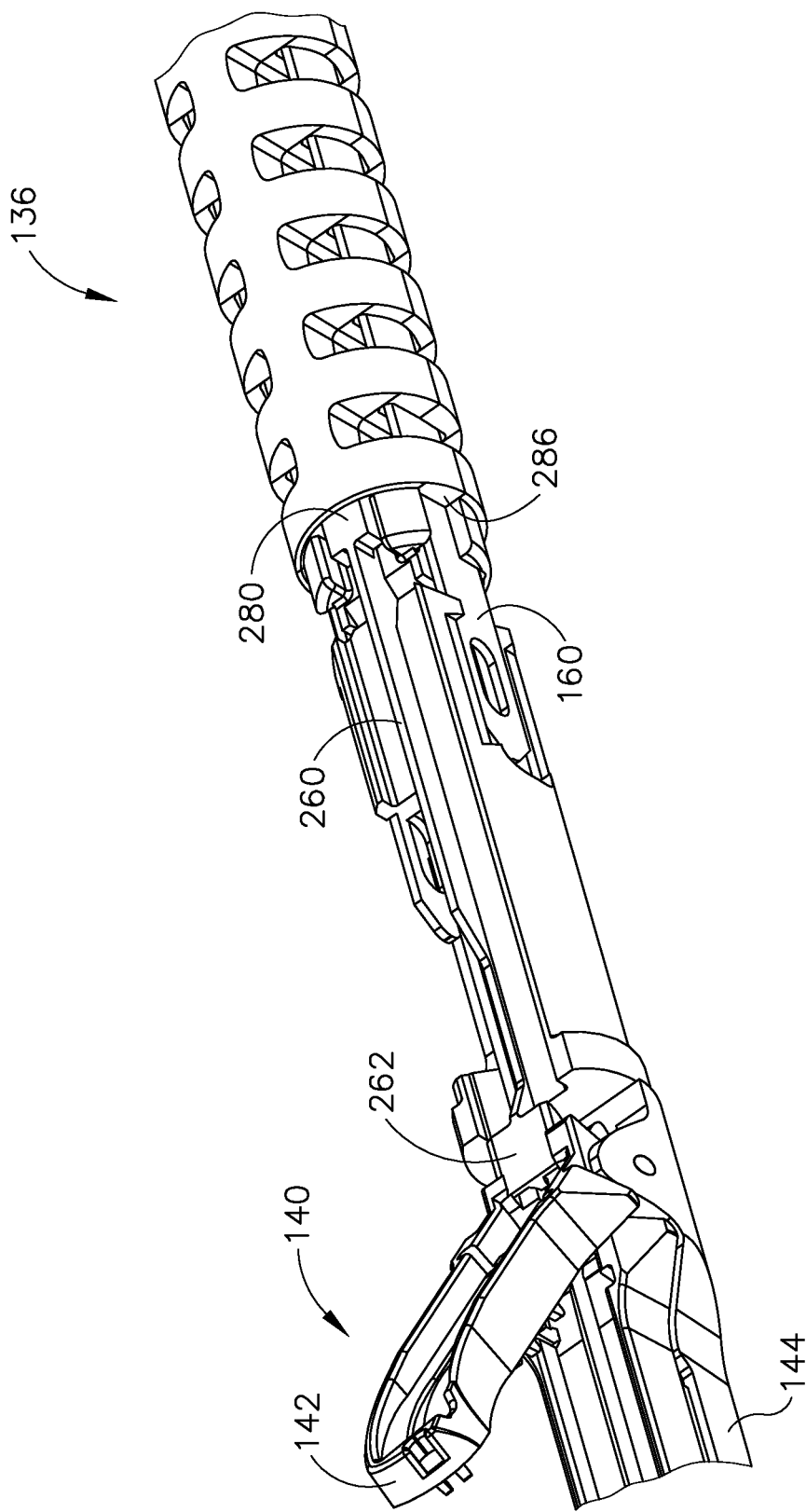
FIG. 19 depicts a perspective view of a stop member of the firing beam assembly of FIG. 18 engaged with the distal end of the articulation section of the device of FIG. 5.

FIGS. 18-19 show an exemplary alternative firing assembly (200) that may be readily incorporated into instrument (10, 100) described above; and/or into various other kinds of instruments. Firing assembly (200) will be discussed below in the context of instrument (100) only, though it should be understood that this context is being used merely as one of many possible examples. Firing assembly (200) of this example comprises a cutting member driver tube (238), a driver block (239), a cutting member driver beam (270), and a cutting member (260). Cutting member driver tube (238) is substantially similar to cutting member driver tube (138) described above. Driver block (239) is substantially similar to driver block (139) described above. Cutting member (260) is substantially similar to cutting member (146) and firing beam (60) described above. All of the foregoing components of firing assembly (200) unitarily translate distally in response to trigger (324) being squeezed toward pistol grip (322); and unitarily translate proximally in response to trigger (324) pivoting away from pistol grip (322).

Figure 20:
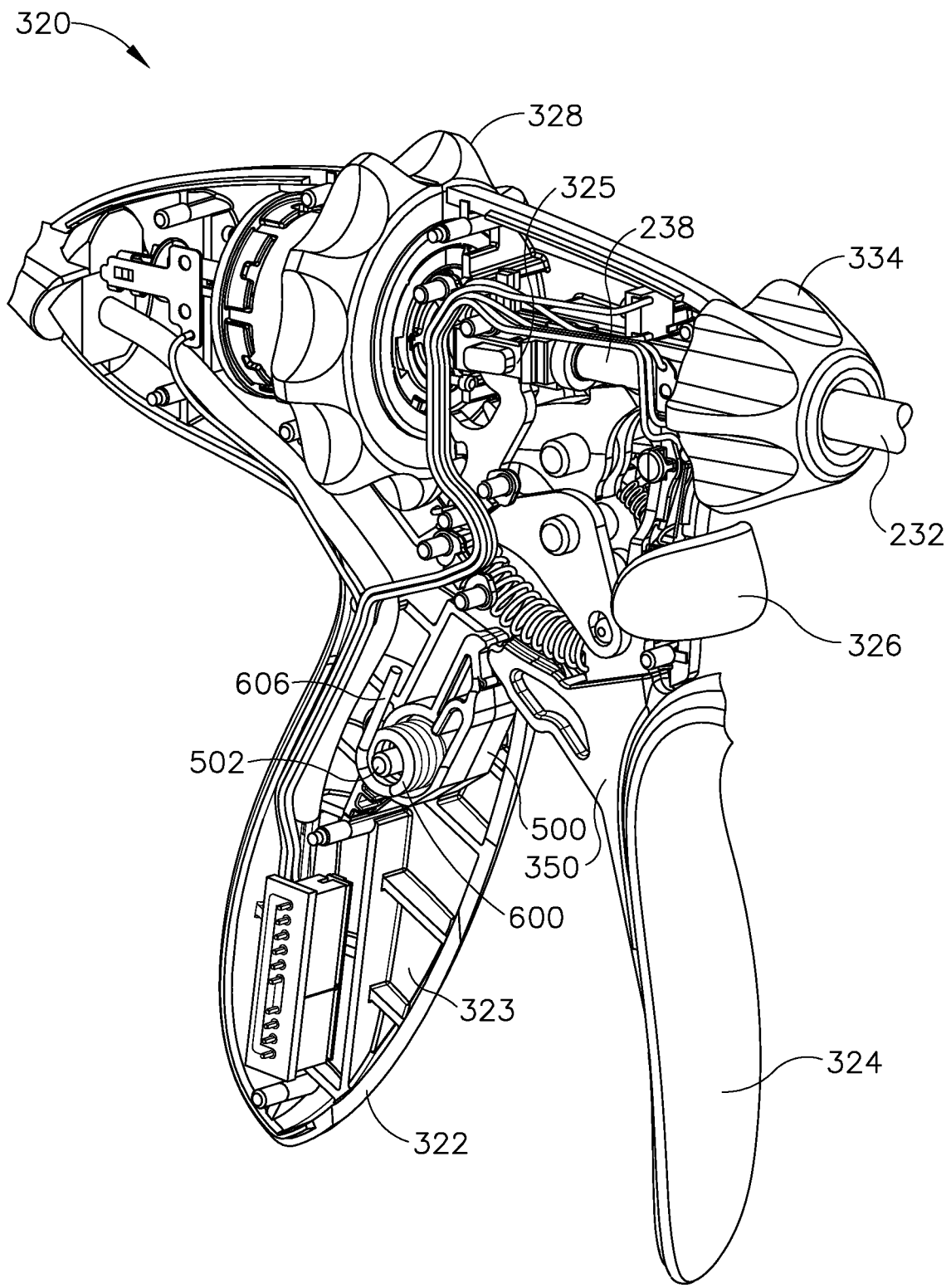
FIG. 20 depicts a perspective view of an exemplary alternative handle assembly, with a right housing half removed, suited for incorporation in the device of FIG. 5.

As shown in FIG. 20, the proximal end of driver tube (238) is coupled with trigger (324) by a yoke (325), which converts pivotal movement of trigger (324) into linear movement of driver tube (238). The distal end of driver tube (238) includes a longitudinally extending slot (242) that receives the proximal end (240) of driver block (239). Proximal end (240) is fixedly secured in slot (242), such as by an interference fit and/or any other suitable type of relationship, etc. Proximal end (240) of driver block (239) is tapered in this example, though it should be understood that other configurations could be used. The distal end (250) of driver block (239) includes a pair of laterally projecting peg members (252, 254). Peg members (252, 254) are received in corresponding openings (272, 274) of driver beam (270). Driver beam (270) is longitudinally positioned to extend through articulation section (136). Driver beam (270) thus has sufficient flexibility and tensile strength to bend with articulation section (136) and still transfer linear actuating forces to cutting member (260) when articulation section (236) is in a bent configuration. Driver beam (270) includes a distal projection (276) that is received in a proximal recess (282) of cutting member (260). Of course, the foregoing features that provide coupling between driver tube (238), driver block (239), driver beam (270), and cutting member (260) are merely exemplary. Various other suitable structures and techniques for coupling these components together will be apparent to those of ordinary skill in the art in view of the teachings herein.

Cutting member (260) of the present example includes an upper flange (262), a lower flange (266), and a distal blade (264). In some versions, cutting member (260) is substantially more rigid than driver beam (270). Flanges (262, 266) and blade (264) of the present example are substantially the same as flanges (62, 66) and blade (64) described above. In other words, flanges (62, 66) are operable to actuate jaws (142, 144) of end effector while distal blade (264) is operable to sever tissue captured between jaws (142, 144). Cutting member (260) of this example also includes a stop member (280). Stop member (280) comprises a block integrally positioned on the upper edge of cutting member (260), located proximal to upper flange (262). As best seen in FIG. 19, stop member (280) is configured to engage a distal face (286) presented by articulation section (136) when firing assembly (200) is in a proximal position, with the jaws (142, 144) of end effector (140) in a fully open configuration. It should be understood that stop member (280) may restrict the proximal positioning of cutting member (260), to thereby ensure a consistent positioning of flanges (262, 266) relative to jaws (142, 144) when firing assembly (200) is in a proximal position. This may prevent flanges (262, 266) from fully disengaging jaws (142, 144) when firing assembly (200) is in a proximal position.

In the present example, a distal sheath section (not shown) encompasses the assembly that extends between articulation section (136) and end effector (140). This distal sheath section is omitted from FIG. 19 in order to show the position of stop member (280). As shown in FIG. 20, driver tube (238) and a proximal portion of driver beam (270) are encompassed within a sheath (232), similar to sheath (132) described above. Sheath (232), firing assembly (200), articulation section (136), and end effector (140) are all rotatable about the longitudinal axis defined by sheath (232), relative to handpiece (320), via a knob (334). Knob (334), sheath (132), articulation section (136), end effector (140), and/or some other component may include a visible marking to enable a surgeon to readily ascertain the angular position of end effector (140) about the longitudinal axis defined by sheath (232). In addition or in the alternative, one or more detent features and/or other kind of feature(s) may provide an audible and/or tactile indication of the angular position of end effector (140) about the longitudinal axis defined by sheath (232). Of course, some versions may also simply lack rotatability altogether, such that knob (334) may be omitted.

B. Exemplary Return Stroke Assist

As noted above, a trigger (24, 124) may be squeezed toward a pistol grip (22, 124) to actuate an end effector (40, 140). In the foregoing examples, a spring (not shown) resiliently biases trigger (24, 124) away from pistol grip (22, 124). Thus, after a user has fully squeezed trigger (24, 124) toward pistol grip (22, 124) to actuate end effector (40, 140), the user may simply release trigger (24, 124), and the spring may then return trigger (24, 124) to a "home" position where it is pivoted away from pistol grip (22, 124). In some versions, friction through articulation section (36, 136) may provide substantial resistance to trigger (24, 124) returning to the home position, particularly when articulation section (36, 136) is in a bent configuration. This resistance may be most pronounced when trigger (24, 124) is near the end of its return stroke. It may therefore be desirable in some instances to provide additional mechanical assistance to trigger (24, 124) as it approaches the end of its return stroke. It may also be desirable to provide a substantially constant amount of resistance to the user squeezing trigger (24, 124) during the entire firing stroke, such that the resistance forces encountered by the user are not substantially greater during certain stages of the firing stroke.

Figure 21A:
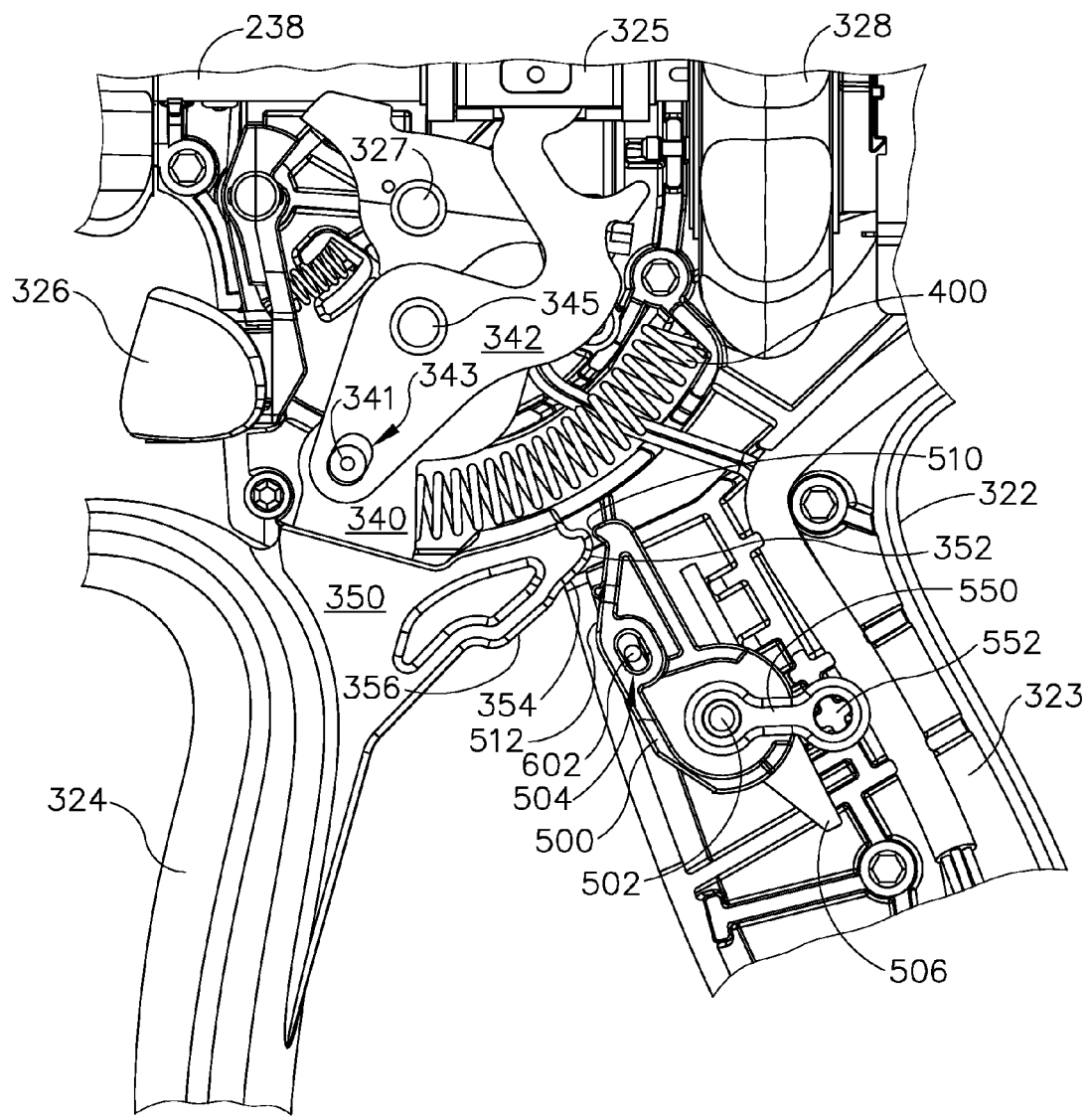
FIG. 21A depicts a side elevational view of the handle assembly of FIG. 20, with a left housing half removed to reveal an exemplary return assist pivoting cam feature in a first position.
Figure 21B:
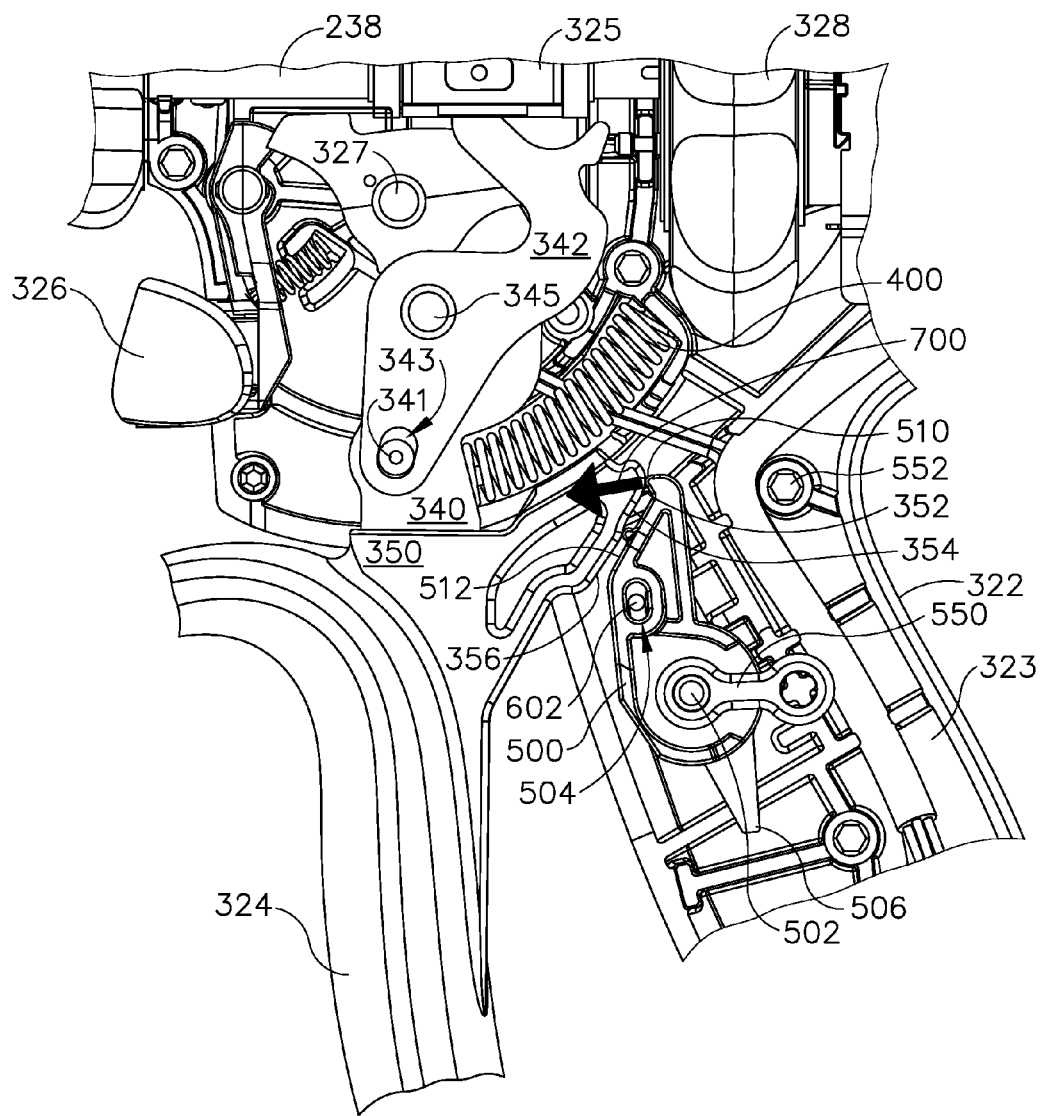
FIG. 21B depicts a side elevational view of the components of FIG. 21A, with the return assist pivoting cam feature in a second position.
Figure 21C:
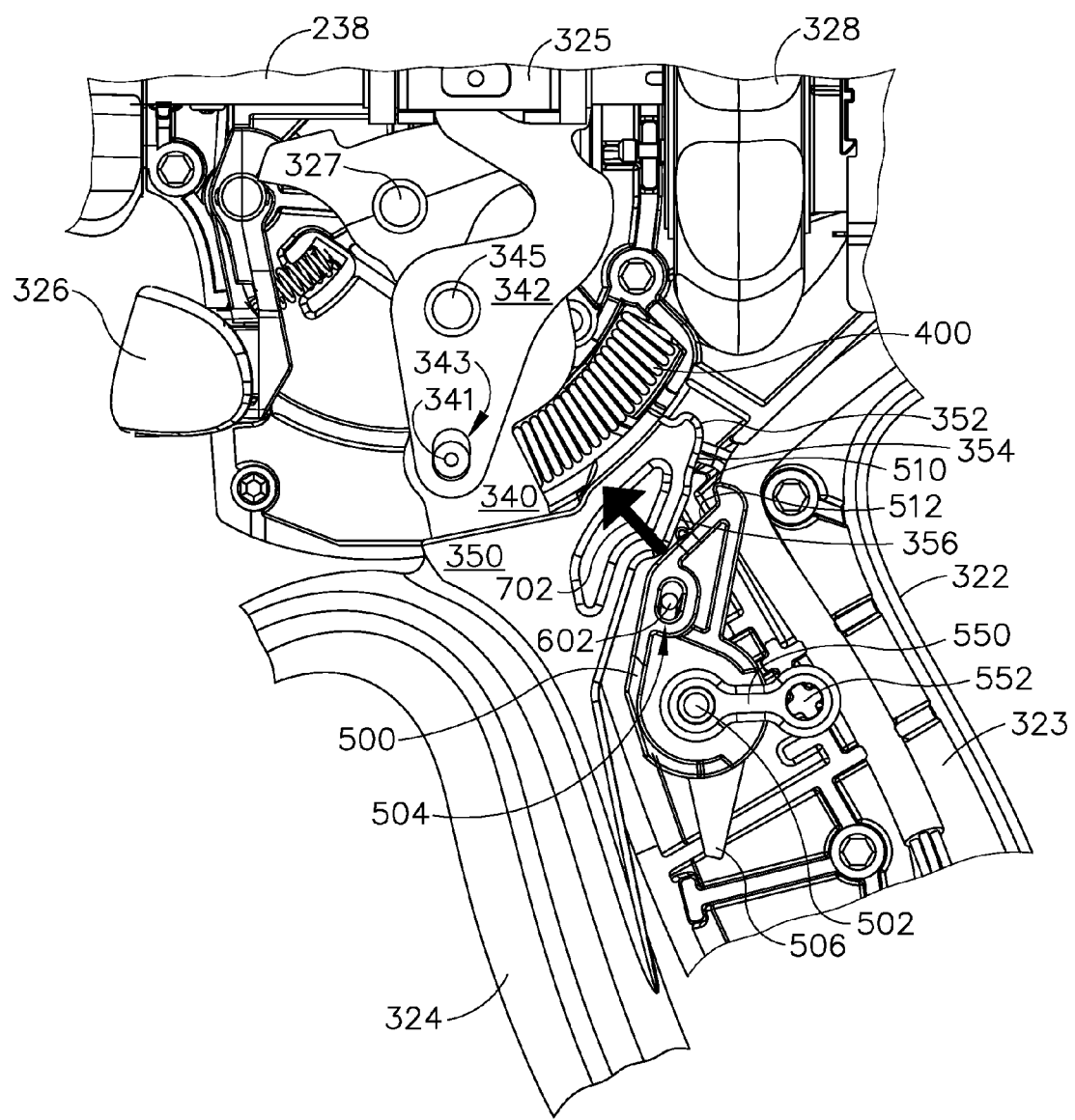
FIG. 21C depicts a side elevational view of the components of FIG. 21A, with the return assist pivoting cam feature in a third position.

FIGS. 20-21C show exemplary components that may be used to assist the return stroke of trigger (24, 124) from an actuated position (e.g., where trigger (24, 124) is pivoted to pistol grip (22, 124)) to a home position (e.g., where trigger (24, 124) is pivoted away from pistol grip (22, 124)). These components may also provide a substantially constant amount of resistance to the user squeezing trigger (24, 124) during the entire firing stroke (e.g., from the home position of FIG. 21A to the actuated position of FIG. 21C). In this example, a trigger (324) is pivotally secured to a housing (323) of a handpiece at a pivot point (327) by a pivot arm (340). Pivot arm (340) is coupled with yoke (325) by a linkage (342). In particular, a pin (341) that is integral with pivot arm (340) is disposed in a slot (343) of linkage (342). Linkage (342) is pivotable about a pivot point (345) that is fixed relative to housing (323). Thus, pivoting of trigger (324) is transmitted to yoke (325) by linkage (342) to translate yoke (325) longitudinally. As noted above, this translation of yoke (325) translates driver tube (238) to translate cutting member (260) longitudinally. A coil spring (400) is disposed between pivot arm (340) and housing (323), and is configured to resiliently bias trigger (324) to the home position shown in FIG. 21A.

Trigger (324) also includes a unitary, proximally extending cam arm (350) that engages a cam lever (500) as will be described in greater detail below. Cam arm (350) includes a tip (352), a first underside surface (354), and a second underside surface (356). Cam arm (350) provides a generally rounded transition from tip (352) to first underside surface (354). Cam arm (350) also provides a sloped or angled transition from first underside surface (354) to second underside surface (356). Surfaces (354, 356) are generally parallel to each other but are offset relative to each other as best seen in FIGS. 21A-21C. The offset of surfaces (354, 356) provides staged engagement with cam lever (500) during actuation of trigger (324).

Cam lever (500) is pivotally secured to housing (323) by a post (502). A torsion spring (600) is coaxially disposed about post (502) and resiliently biases cam lever (500) to the rotational position shown in FIG. 21A. As shown in FIG. 20, torsion spring (600) includes a first free end (602) that engages a boss (not shown) of housing (323), thereby providing a mechanical ground for torsion spring (600). First free end (602) is substantially straight and extends generally parallel to the longitudinal axis defined by pistol grip (322). As shown in FIGS. 21A-21C, torsion spring (600) also includes a second free end (604) that is disposed in a slot (504) of cam lever (500). Second free end (604) is generally bent and extends transversely relative to the longitudinal axis defined by pistol grip (322). A brace (550) is secured to post (502) and another post (552). Brace (550) simply retains cam lever (500) relative to housing (323), such as to prevent cam lever (500) from disengaging post (502) during assembly. Brace (550) does not affect rotation of cam lever (500) relative to housing (323).

In the present example, torsion spring (600) is pre-loaded in the configuration shown in FIG. 21A, urging cam lever (500) counterclockwise. Cam lever (500) includes a grounding arm (506) that engages and bears against a boss (not shown) of housing (323) when cam lever (500) is in the position shown in FIG. 21A. Grounding arm (506) thus provides a rotational stop for cam lever (500), preventing cam lever (500) from pivoting further counterclockwise from the position shown in FIG. 21A under the load of torsion spring (600). As cam lever (500) pivots clockwise from the position shown in FIG. 21A toward the position shown in FIG. 21C, torsion spring (600) resists such rotation and continues to provide a counterclockwise bias to cam lever (500).

Cam lever (500) also includes a free end (510) and bearing surface (512) that engage the underside of cam arm (350) at various positions depending on the rotational position of trigger (324) during the transition from the configuration shown in FIG. 21A to the configuration shown in FIG. 21C. In particular, free end (510) is initially spaced from tip (352) of cam arm (350) when trigger (324) is in the home position shown in FIG. 21A. In some other versions, free end (510) contacts tip (352) at this stage. The gap between free end (510) and tip (352) in the present example is nevertheless very small, such that tip (352) almost immediately contacts free end (510) when the user begins to pivot trigger (324) toward pistol grip (322).

During a first phase of the firing stroke of trigger (324), transitioning from the configuration shown in FIG. 21A to the configuration shown in 21B, free end (510) bears against tip (352) and then slides along first underside surface (354). The bias from torsion spring (600) is transmitted to trigger (324), such that the user may feel the resistance from torsion spring (600) via the trigger (324). This is due to the force vectors from torsion spring (600) being oriented generally tangential (e.g., within approximately 45° of a tangent) to the arcuate path of trigger (324) and/or being substantially non-parallel (e.g., greater than approximately 45° deflection) relative to a radius extending from pivot point (327) to the point of engagement between lever arm (500) and cam arm (350) during the first phase. An exemplary force vector at this stage is shown as arrow (700) in FIG. 21B and represents the force exerted by torsion spring (600) on trigger (324) via lever arm (500).

In the present example, this first phase of the firing stroke is provided through the first approximately 15° of rotation, the first approximately 16° of rotation, or the first approximately 17° of rotation of trigger (324) from a home position (FIG. 21A) to a partially actuated position (FIG. 21B). Of course, any other suitable angular range may define a first phase of the firing stroke of trigger (324). It should be understood from the foregoing that coil spring (400) cooperates with torsion spring (600) to bias trigger (324) clockwise during the first phase of the firing stroke of trigger (324).

Upon completion of the first phase of the firing stroke of trigger (324), a second phase begins where free end (510) disengages first underside surface (354) and bearing surface (512) engages second underside surface (356) of cam arm (350). In the present example, the second phase includes the transition from a configuration following at some point in time after the configuration shown in FIG. 21B to the configuration shown in FIG. 21C. During the second phase, the bias from torsion spring (600) is still transmitted to trigger (324), though the user will either no longer feel the resistance from torsion spring (600) via the trigger (324) or such resistance will be substantially reduced during the second phase. This is due to the force vectors from torsion spring (600) being oriented generally parallel (e.g., within approximately 45° degrees) relative to a radius extending from pivot point (327) to the point of engagement between lever arm (500) and cam arm (350) during the second phase. In other words, most if not all of the forces from torsion spring (600) are transmitted via trigger (324) to pivot point (327), such that the forces are ultimately borne by housing (323). An exemplary force vector at this stage is shown as arrow (702) in FIG. 21C and represents the force exerted by torsion spring (600) on trigger (324) via lever arm (500).

Of course, the user may still feel resistance through trigger (324) due to bias provided by coil spring (400), friction within the drive train of cutting member (260), resistance provided by tissue in end effector (140), etc. during the second phase. The second phase may end when cutting member (260) reaches a fully distal position, completing the firing stroke. In some versions, trigger (324) has rotated approximately 33° from the home position to fully complete the firing stroke. The force exerted by torsion spring (600) on trigger (324) via lever arm (500) may continue to be oriented generally parallel (e.g., within approximately 45° degrees) relative to a radius extending from pivot point (327) to the point of engagement between lever arm (500) and cam arm (350) upon completion of the second phase (e.g., upon completion of the firing stroke).

After completing the firing stroke the user may release trigger (324) to return trigger (324) from the actuated position back to the home position and to open jaws (142, 144) of end effector (140). In some instances, this is done to separate tissue structures that are positioned on the outside of jaws (142, 144), to perform a blunt dissection of tissue, and/or for other purposes. Coil spring (400) provides a bias to rotate trigger (324) clockwise from the position shown in FIG. 21C to the position shown in FIG. 21B after the use releases trigger (324) at the end of the firing stroke. Torsion spring (600) does not provide a significant bias or assistance during this stage. However, once trigger (324) reaches the position shown in FIG. 21B (e.g., when trigger (324) is approximately 15°, approximately 16°, or approximately 17° from the home position) during the return stroke, free end (510) and/or bearing surface (512) may once again bear against cam arm (350), thereby providing an additional clockwise bias to trigger (324). In some instances, the frictional forces within the drive train of cutting member (260) may be relatively high during the transition from the configuration shown in FIG. 21B to the configuration shown in FIG. 21A, such that the additional bias from torsion spring (600) helps to counteract these additional frictional forces. The end result may be a substantially smooth transition from the configuration shown in FIG. 21C to the configuration shown in FIG. 21A, without increases in frictional forces prematurely halting or significantly slowing the return of trigger (324) from the fully actuated position to the home position. Of course, any other suitable components, features, and configurations may be used to assist return of trigger (324) to a home position. Alternatively, such components may simply be omitted if desired.

While the example described above includes a pistol grip (322), it should be understood that the foregoing teachings may be readily applied to devices having various other kinds of grips. By way of example only, a variation of trigger (324) and cam lever (500) may be provided in accordance with the above teachings in a device having a scissor grip. Other kinds of grips that may be combined with the above teachings will be apparent to those of ordinary skill in the art. Furthermore, a variation of trigger (324) and cam lever (500) may be readily incorporated into devices having various other kinds of end effectors, including but not limited to tissue graspers, tissue retrieval pouch deploying instruments, surgical staplers, ultrasonic surgical instruments, etc.

It should be understood that any of the devices herein may also include one or more of the various features disclosed in U.S. Pub. No. 2012/0078243, entitled "Control Features for Articulating Surgical Device," published Mar. 29, 2012, the disclosure of which is incorporated by reference herein; U.S. Pub. No. 2012/0078244, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, the disclosure of which is incorporated by reference herein; U.S. Pub. No. 2012/0078248, entitled "Articulation Joint Features for Articulating Surgical Device," published Mar. 29, 2012, the disclosure of which is incorporated by reference herein; and/or U.S. patent application Ser. No. 13/622,735, entitled "Surgical Instrument with Contained Dual Helix Actuator Assembly," filed Sep. 19, 2012, published as U.S. Pub. No. 2013/0023868 on Jan. 24, 2013, the disclosure of which is incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

V. Miscellaneous

While the examples herein are described mainly in the context of electrosurgical instruments, it should be understood that the teachings herein may be readily applied to a variety of other types of medical instruments. By way of example only, the teachings herein may be readily applied to tissue graspers, tissue retrieval pouch deploying instruments, surgical staplers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
   (a) an end effector, wherein the end effector is operable to grasp tissue;
   (b) an elongate shaft having a distal end and a proximal end, wherein the end effector is positioned at the distal end of the shaft;
   (c) a handle assembly associated with the proximal end of the shaft, wherein the handle assembly comprises:
      (i) a body portion,
      (ii) a trigger movable relative to the body portion, wherein the trigger is operable to control the end effector to selectively grasp tissue, wherein the trigger is movable from a home position to an actuated position, wherein the trigger includes a cam feature,
      (iii) a trigger return lever positioned to engage the cam feature of the trigger,
      (iv) a first biasing member coupled with the trigger and the body portion, wherein the first biasing member is configured to bias the trigger toward the home position during at least part of a range of motion of the trigger from the home position to the actuated position, and
      (v) a second biasing member coupled with the trigger return lever and the body portion, wherein the second biasing member is configured to bias the trigger return lever toward the trigger.

2. The apparatus of claim 1, wherein the body portion comprises a grip, wherein the trigger is pivotable toward the grip to move from the home position to the actuated position.

3. The apparatus of claim 2, wherein the grip comprises a pistol grip.

4. The apparatus of claim 1, wherein the cam feature comprises a proximally extending cam arm.

5. The apparatus of claim 4, wherein the cam arm includes a tip and an underside, wherein the trigger return lever comprises a free end and a bearing surface, wherein the free end of the return lever is configured to engage at least the tip of the cam arm, wherein the bearing surface of the return lever is configured to engage the underside of the cam arm.

6. The apparatus of claim 5, wherein the trigger is movable from the home position to an intermediate position between the home position and the actuated position, wherein the free end of the trigger return lever is configured to engage the tip and the underside of the cam arm during travel of the trigger from the home position to the intermediate position.

7. The apparatus of claim 6, wherein the bearing surface of the trigger return lever is configured to engage the underside of the cam arm during travel of the trigger from the intermediate position to the actuated position.

8. The apparatus of claim 7, wherein the free end of the trigger return lever is configured to disengage the cam arm during travel of the trigger from the intermediate position to the actuated position.

9. The apparatus of claim 5, wherein the underside of the cam arm includes a first underside surface and a second underside surface, wherein the first and second underside surfaces are offset relative to each other.

10. The apparatus of claim 1, wherein the first biasing member comprises a coil spring.

11. The apparatus of claim 10, wherein the second biasing member comprises a torsion spring.

12. The apparatus of claim 1, wherein the end effector comprises a pair of jaws, wherein at least one of the jaws is pivotable toward the other jaw, wherein the trigger is operable to control the jaws.

13. The apparatus of claim 1, wherein the end effector comprises at least one electrode operable to deliver RF energy to tissue.

14. The apparatus of claim 1, wherein the end effector comprises a translating cutting member, wherein the trigger is further operable to translate the cutting member.

15. The apparatus of claim 1, wherein the shaft defines a longitudinal axis, wherein the shaft includes an articulation section, wherein the articulation section is operable to selectively deflect the end effector away from the longitudinal axis of the shaft.

16. The apparatus of claim 15, further comprising a translatable member extending from the handle assembly to the end effector and through the shaft, wherein the trigger is operable to translate the translatable member relative to the shaft.

17. The apparatus of claim 16, wherein the translatable member includes a stop feature operable to engage a distal portion of the articulation section of the shaft, wherein the stop feature is operable to restrict proximal positioning of the translatable member relative to the articulation section.

18. An apparatus, comprising:
   (a) an end effector, wherein the end effector is operable to operate on tissue;
   (b) an elongate shaft having a distal end and a proximal end, wherein the end effector is positioned at the distal end of the shaft;
   (c) a handle assembly associated with the proximal end of the shaft, wherein the handle assembly comprises:
      (i) a body portion,
      (ii) a trigger movable relative to the body portion, wherein the trigger is operable to control the end effector, wherein the trigger is movable through a first range of motion from a home position to an intermediate position, wherein the trigger is further movable through a second range of motion from the intermediate position to an actuated position, and
      (iii) a trigger return lever positioned to engage a portion of the trigger,
      (iv) a first biasing member coupled with the trigger and the body portion, wherein the first biasing member is configured to bias the trigger toward the home position during the first range of motion, (v) a second biasing member coupled with the trigger return lever and the body portion, wherein the second biasing member is configured to bias the trigger return lever toward the trigger.

19. The apparatus of claim 18, wherein the trigger is pivotable along an arc defined by a radius, wherein the trigger return lever is configured to bear against the trigger with a force oriented generally tangentially relative to the arc during the first range of motion, wherein the trigger return lever is configured to bear against the trigger with a force oriented generally parallel to the radius during the second range of motion.

20. An apparatus, comprising:
(a) a body;
(b) an end effector comprising:
 (i) a first jaw, and
 (ii) a second jaw,
 wherein the first jaw is movable toward the second jaw to clamp tissue between the first and second jaw,
 wherein at least one of the jaws comprises at least one electrode,
 wherein the at least one electrode is operable to deliver RF energy to tissue clamped between the first and second jaw;
(c) a cutting member operable to cut tissue clamped between the first jaw and the second jaw;
(d) a shaft extending between the body and the end effector;
(e) a trigger operable to actuate the cutting member, wherein the trigger includes a cam arm;
(f) a first biasing member coupled with the trigger and the body;
(g) a trigger return lever engaged with the cam arm, wherein the first biasing member is configured to bias the trigger to a home position; and
(h) a second biasing member coupled with the trigger return lever and the body, wherein the second biasing member is configured to bias the trigger return lever toward the trigger.

* * * * *